US008998472B2

(12) United States Patent
Johanson

(10) Patent No.: US 8,998,472 B2
(45) Date of Patent: Apr. 7, 2015

(54) LIQUID FILLED LIGHT GUIDE CONTAINING VOIDS WITHIN THE WALLS

(76) Inventor: Walter A Johanson, Camarillo, CA (US)

( * ) Notice: Subject to any disclaimer, the term of this patent is extended or adjusted under 35 U.S.C. 154(b) by 498 days.

(21) Appl. No.: 13/498,557

(22) PCT Filed: May 4, 2010

(86) PCT No.: PCT/US2010/001332
§ 371 (c)(1),
(2), (4) Date: Mar. 27, 2012

(87) PCT Pub. No.: WO2010/129047
PCT Pub. Date: Nov. 11, 2010

(65) Prior Publication Data
US 2012/0182719 A1   Jul. 19, 2012

Related U.S. Application Data

(60) Provisional application No. 61/265,485, filed on Dec. 1, 2009, provisional application No. 61/259,775, filed on Nov. 10, 2009, provisional application No. 61/215,368, filed on May 4, 2009.

(51) Int. Cl.
G02B 6/032 (2006.01)
A01G 7/04 (2006.01)
C12M 1/00 (2006.01)
G02B 6/26 (2006.01)
G02B 6/42 (2006.01)

(52) U.S. Cl.
CPC .............. A01G 7/045 (2013.01); C12M 21/02 (2013.01); C12M 31/08 (2013.01); G02B 6/262 (2013.01); G02B 6/4298 (2013.01)

(58) Field of Classification Search
USPC .............. 362/558, 559, 560, 562, 576, 578; 385/125
See application file for complete search history.

(56) References Cited

U.S. PATENT DOCUMENTS

| | | | | |
|---|---|---|---|---|
| 1,232,047 A | * | 7/1917 | Klotz | 362/562 |
| 3,441,957 A | | 4/1969 | Friedman | |
| 3,740,113 A | * | 6/1973 | Cass | 385/125 |
| 3,890,497 A | * | 6/1975 | Rush | 362/473 |
| 4,009,382 A | * | 2/1977 | Nath | 362/582 |
| 4,195,907 A | * | 4/1980 | Zamja et al. | 385/125 |
| 4,952,511 A | | 8/1990 | Radmer | |

(Continued)

OTHER PUBLICATIONS

International Search Report prepared by the U.S. Patent and Trademark Office on Jun. 28, 2010, for International Application No. PCT/US10/01332.

(Continued)

Primary Examiner — Ismael Negron
(74) Attorney, Agent, or Firm — Tope-Mckay & Associates

(57) ABSTRACT

Illumination systems that include a plurality of illumination devices disposed within a water environment. Such illumination devices having a tube filled with water, at least one light source positioned to project light into the tube, and connected to the illumination devices via light carrying connectors, include one or more voids within each tube wall which extend substantially longitudinally and cause light incident below a critical angle to be reflected back into the tube. Projected or reflected light above a critical angle that strikes a portion of the wall without a void is transmitted through the tube wall. By adjusting the ratio of voids to non-voids light can be delivered in a controlled manner.

6 Claims, 28 Drawing Sheets

(56) References Cited

U.S. PATENT DOCUMENTS

| | | | |
|---|---|---|---|
| 5,104,803 A | 4/1992 | Delente | |
| 5,412,750 A * | 5/1995 | Nath | 385/125 |
| 5,799,124 A * | 8/1998 | Zorn et al. | 385/125 |
| 5,857,761 A * | 1/1999 | Abe et al. | 362/551 |
| 5,982,969 A * | 11/1999 | Sugiyama et al. | 385/125 |
| 6,030,108 A | 2/2000 | Ishiharada et al. | |
| 6,314,226 B1 * | 11/2001 | Nath | 385/125 |
| 6,621,973 B1 | 9/2003 | Hoffman | |
| 8,136,959 B2 * | 3/2012 | Ho | 362/223 |
| 2004/0222163 A1 | 11/2004 | Saccomano | |
| 2005/0181195 A1 | 8/2005 | Dubrow | |
| 2006/0104582 A1 | 5/2006 | Frampton et al. | |
| 2008/0037943 A1 | 2/2008 | Lee et al. | |
| 2009/0105546 A1 | 4/2009 | Hestad et al. | |

OTHER PUBLICATIONS

International Preliminary Report on Patentability (Chapter I) prepared by the U.S. Patent and Trademark Office on Nov. 17, 2011, for International Application No. PCT/US10/01332.

* cited by examiner

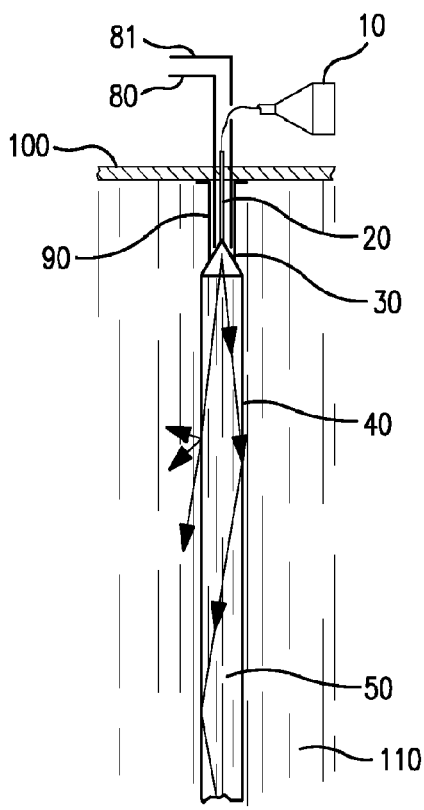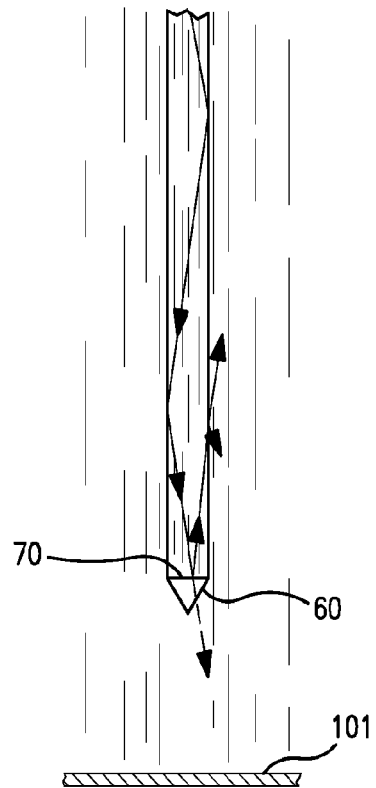
FIG. 1

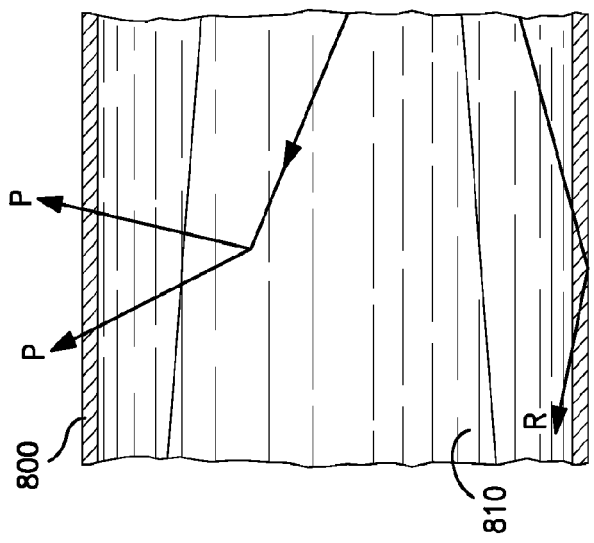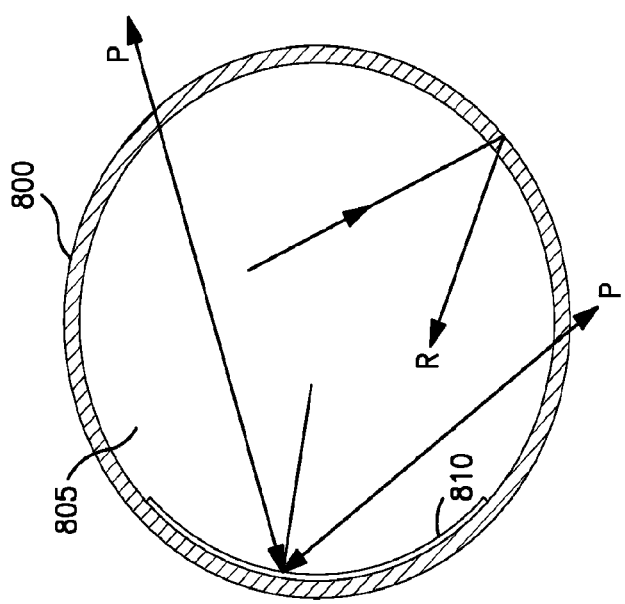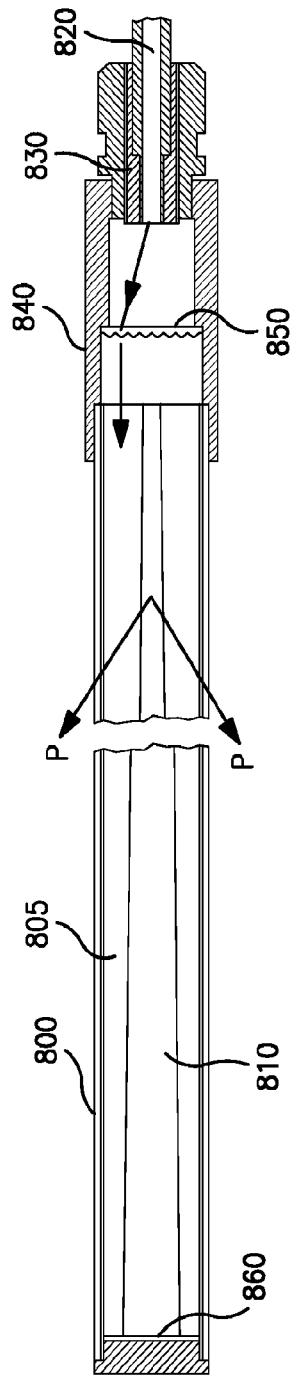
FIG. 24
FIG. 23
FIG. 22

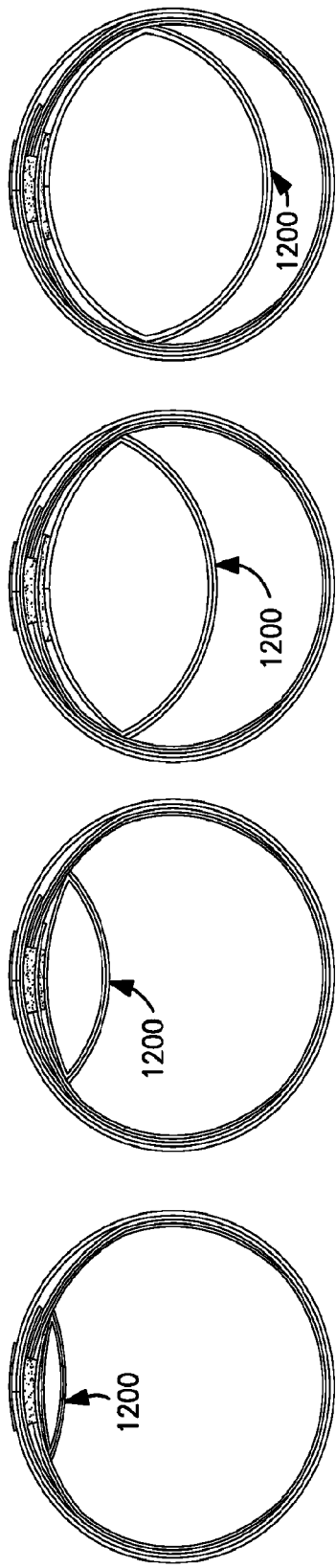
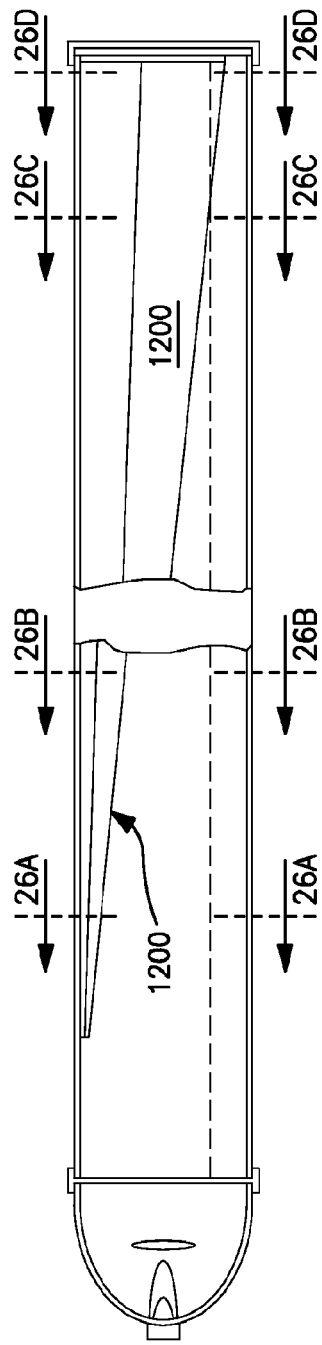

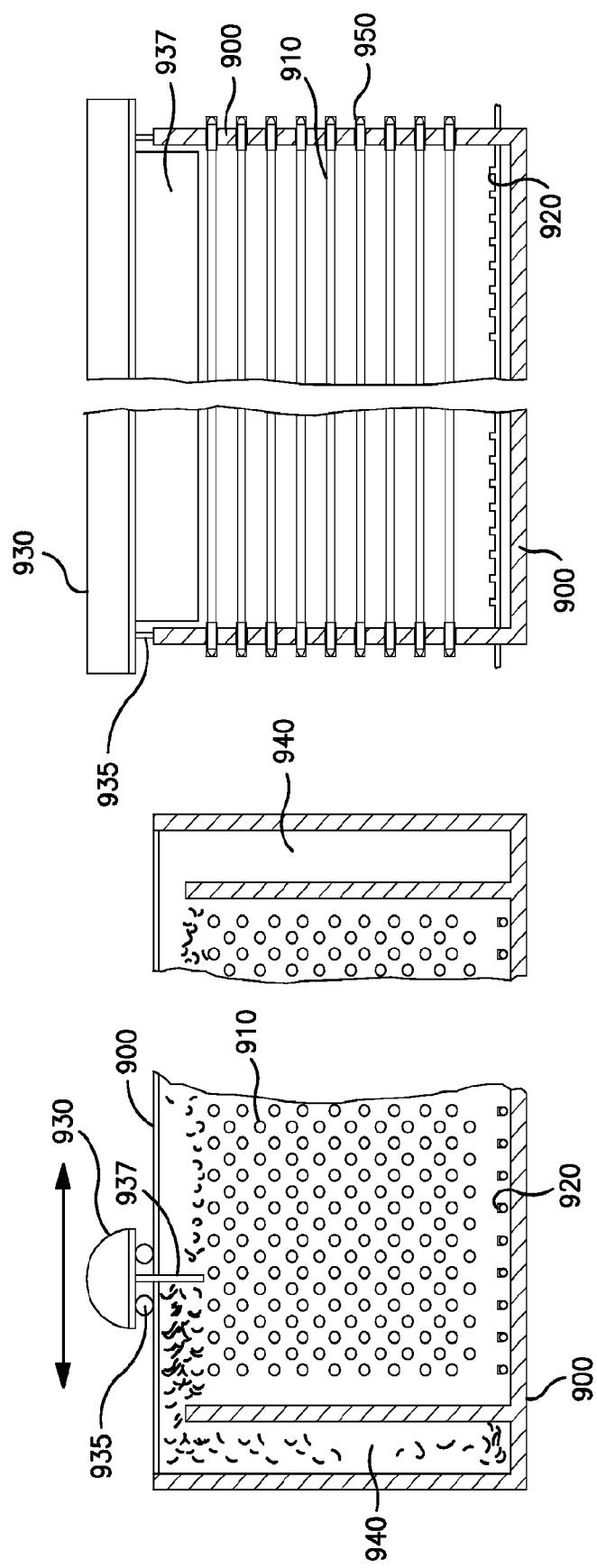

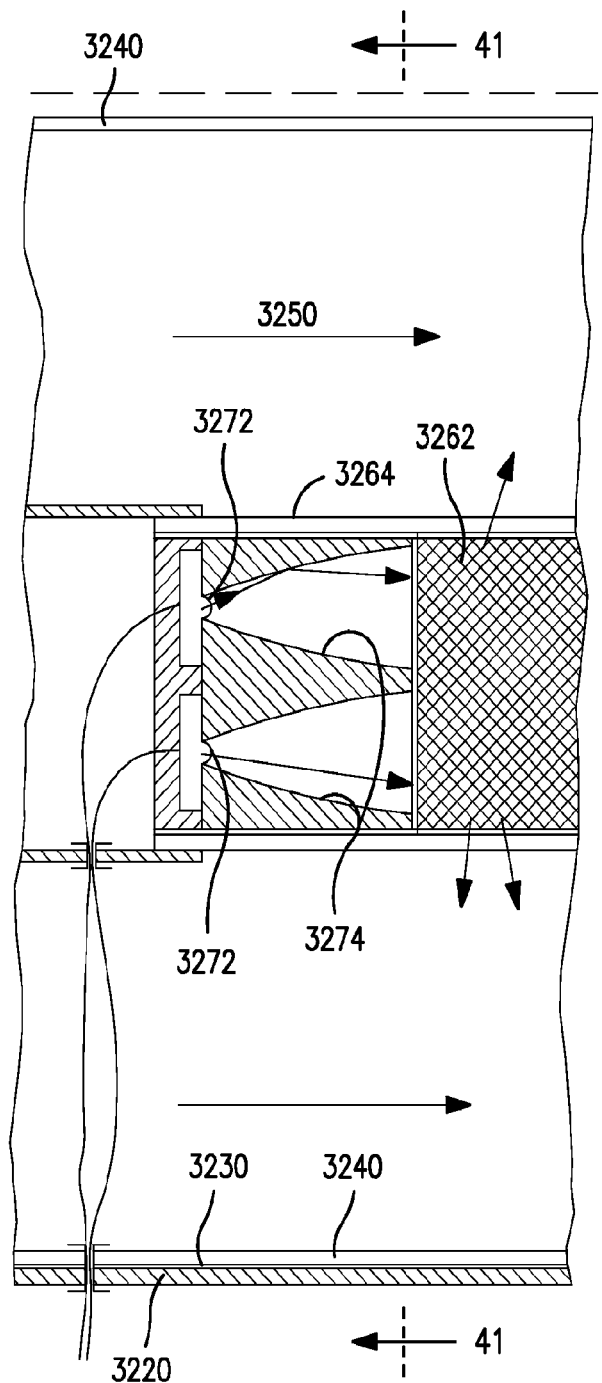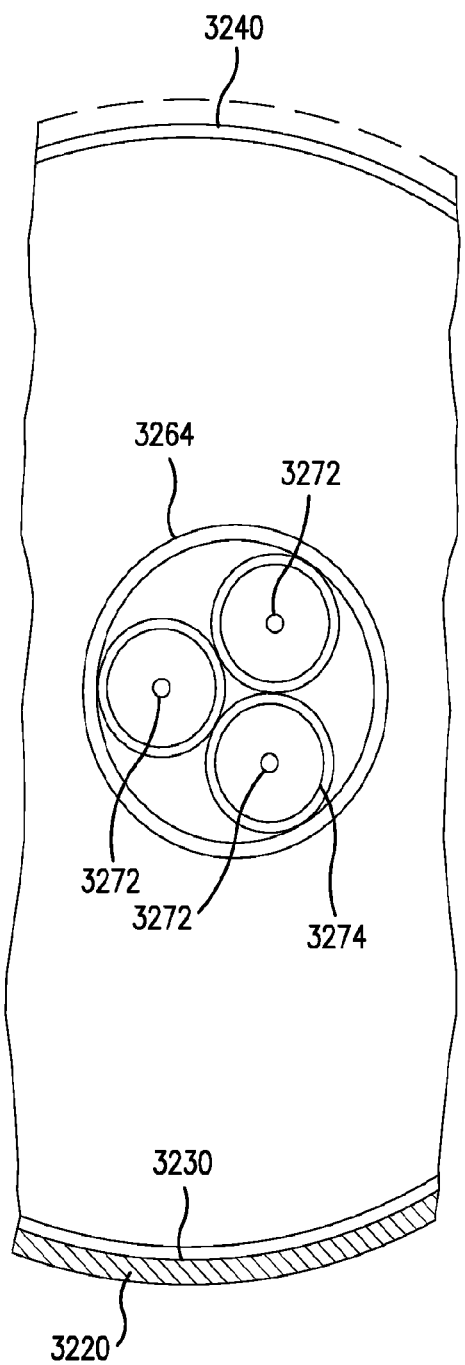
FIG. 40     FIG. 41

LIQUID FILLED LIGHT GUIDE CONTAINING VOIDS WITHIN THE WALLS

RELATED APPLICATION DATA

This application claims the benefit of U.S. provisional patent applications 61/215,368 filed on May 4, 2009, 61/259,775 filed on Nov. 10, 2009 and 61/265,485 filed on Dec. 1, 2009.

The present invention is directed to illumination devices and systems for providing dense illumination to submerged environments, such as water environments in large tanks designed to grow algae and consume carbon dioxide.

BACKGROUND OF THE INVENTION

The growth of algae is receiving a significant amount of attention due to its perceived uses as a source of combustible fuel, a source of nourishment, and as a raw material for biodegradable plastics, a consumer of carbon dioxide which is widely viewed as a threat to the environment. Most forms of algae require light to thrive. In light of the anticipated demand for algae, it would be preferable to grow algae in large tanks, for example tanks having a diameter of about 80 meters and a height of about 20 meters. If such tanks are intended to grow algae on a continuous basis, there is a need to supply light throughout the interior of the tank. Light simply directed on the top or outside surfaces of the tank, even if the tank was formed of a transparent material, would be inadequate since the algae close to the surface and sidewalls of the tank would block infiltration of light into the interior of the tank. Improved devices and illumination systems for providing illumination to submerged environments, e.g. bioreactors, are needed.

SUMMARY OF THE INVENTION

The illumination devices and systems of the present invention are designed to withstand hydraulic pressure at virtually any depth, e.g. in excess of 20 meters, and to provide illumination from substantially the entire length of an illumination device which is positioned in a submerged environment. Some embodiments of the present invention utilize light tubes which are substantially filled with water or other suitable liquid. The illumination emanating from the illumination devices of the present invention may or may not have the same intensity over the length of the illumination device. The amount of illumination emitted at various sections can be controlled.

One system of the present invention comprises a plurality of illumination devices disposed within a water environment. At least one and preferably a plurality of sources of illumination are preferably positioned outside of the water environment and are connected to the illumination devices via light carrying connectors, e.g. fiber optic cables or light transport pipes. The illumination devices comprise one or more extractors which collectively extend substantially the entire length of the illuminated devices and to cause the device to emit light over substantially their entire lengths. The extractors reflect light at an angle above a critical angle of incidence so that the reflected light is transmitted through the tube wall(s).

Preferred illumination devices of the present invention are generally hollow tubes filled with a clear liquid, such as water, silicone oil or mineral oil.

According to another embodiment of the present invention, the tubular portions of illumination devices are formed in segments which are substantially connected end to end. Different segments are provided with different structures. Specifically, according to one embodiment, different segments of a single illumination tube are provided with different amounts of surface areas comprising air-to-other-material interfaces. As described in greater detail below, light striking areas having air-to-other-material interfaces will be reflected back into the interior of the tube if the angle of incidence is below a certain critical angle.

According to other embodiments of illumination devices, extractors are positioned within the interior of the tube and/or in or on a surface of the tube in order to reflect light at an angle greater than a critical angle of incidence in order to direct light into the water environment outside of the tube.

Light emanating from the tube into the water environment in which the illumination tube is positioned can be used for the growth of organisms, such as algae. The use of liquid filled tubes can provide an illumination system which has a weight and internal pressure similar to the pressure of the intended submerged environment thereby minimizing or eliminating the pressure difference between the exterior (submerged environment) and the tube interior. Other methods, such as the use of pressurized air, may be utilized to minimize the pressure difference between the pressure inside the tube sidewall and the pressures inside or exterior to the tube.

At least the exterior surfaces of the tubes are preferably either formed of or coated with a nonstick coating, such as Teflon® FEP material.

BRIEF DESCRIPTION OF THE DRAWINGS

FIG. 1 is a side view of a single illumination device suspended in a water environment within a tank.

FIG. 22 is a longitudinal cross-sectional, segmented view of a liquid filled light distribution tube of one embodiment of the present invention.

FIGS. 23 and 24 are partial top and side cross-sectional views, respectively, of the light distribution tube illustrated in FIG. 24.

FIG. 25 is a longitudinal sectional view of a light distribution tube and a light source.

FIGS. 26A through 26D are a succession of cross-sectional views of the light distribution tube shown in FIG. 25 showing the changing configuration of the 3-dimensional light distributor within the light distribution tube.

FIGS. 27 and 28 are cross-sectional, segmented views of one embodiment of a continuous bioreactor of the present invention.

FIG. 40 is a close up view of a portion of a still further embodiment.

FIG. 41 is a cross-sectional view taken along lines 41-41 of FIG. 40.

DETAILED DESCRIPTION

Figure 2:
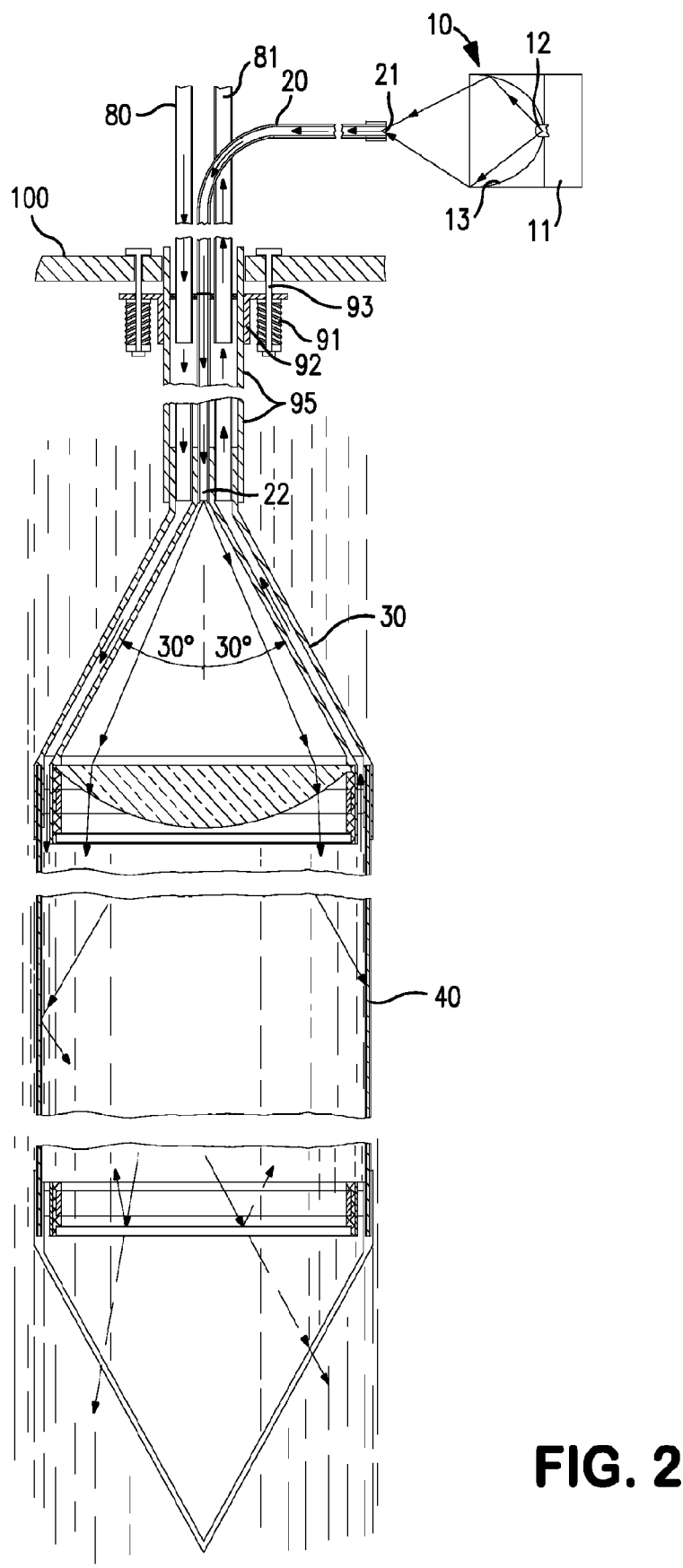
FIG. 2 is a longitudinal cross-sectional, segmented view of the main components of the illumination device shown in FIG. 1.

Various embodiments of the present invention are directed to illumination devices and systems for providing high density illumination in submerged environments. For example, the environments may comprise large bioreactors comprising tanks filled with water in which algae is growing and into which carbon dioxide is provided. While certain embodiments of the present invention and certain figures focus on a single illumination device comprising a single light tube, the illumination systems of the present invention may comprise many illumination devices spaced by distances equal to or less than the diameter of the illumination tube itself. Therefore, large tanks used to grow algae may comprise hundreds or thousands of the disclosed illumination devices. For example, if only one tube is used in each square meter of the cross section of a circular cylindrical tank having a diameter of 80 meters, approximately 5,000 tubes extending the full depth of the tank would be required. Closer positioning, i.e. increasing the density of the illumination tubes and therefore providing more illumination, will increase the number of illumination devices needed. According to other embodiments of the present invention, at least some tubes in an illumination system are positioned at different depths and do not extend substantially the full depth of the tank. For example, it may be desirable to provide more illumination in the top portion of a tank where algae may be present in a higher concentration or density.

FIG. 1 illustrates a single light illumination tube of the present invention positioned within a water environment in a large tank. As used herein, the term "water environment" is used to indicate an environment comprising liquid water and may also comprise other components such as algae, other liquids and/or gases, either in solution and/or in a suspension with the water. One embodiment of the present invention utilizes a large number of illumination devices positioned, preferably generally vertically, within a tank containing a water environment comprising algae and carbon dioxide. In other embodiments described below, the light distributing tubes are not positioned vertically, but are generally horizontal.

With reference to FIG. 1, this embodiment comprises a light source 10 connected to a light injector housing 30 by a fiber optic cable 20. The light injector housing can optionally be provided with a lens for collimating the light and/or filtering the light as desired. This embodiment also comprises a tube 40 substantially filled with a liquid 50, e.g. distilled water. A transparent, conical end cap 60 is positioned at the bottom of tube 40 in this illustrated embodiment. While the illustrated end cap is preferably transparent and conical, the end cap need not be transparent and can have other shapes. In this embodiment where the bottom of the tube 40 is spaced somewhat from the bottom of the tank 101, a transparent end cap advantageously allows illumination of the water environment in the area generally below the illumination device. The tube 40 of FIG. 1 is suspended from the top of the tank 100 by support 90. In this illustrated embodiment, the entire illumination portion is submerged in the water environment 110. A mirror or partial mirror 70 is provided proximate the end cap 60 in order to reflect light back up into tube 50. This embodiment also advantageously comprises a fluid feed tube 80 and a fluid egress tube 81 which connect with an ingress port and an egress port, respectively, and which are used to fill and maintain the level of water in tube 40. The structural details of various embodiments of tube 40 are described below in connection with other figures.

FIG. 2 shows some additional detail of the illumination device and tank of FIG. 1. With reference to FIG. 2, the illustrated light source 10 comprises a housing 11, a bulb 12 and a reflector 13, e.g. an elliptical reflector, which directs light onto the proximal end 21 of fiber optic cable 20 as indicated by the dashed arrowed lines. Since a major portion of the tube 40 will be filled with water according to this embodiment, and since tube 40 may have a diameter of, for example, about 6 to 10 inches and a length of, for example, 18 meters, the water filled tube would be very heavy and would require special handling. Therefore, it is desirable to fill tube 40 while the bioreactor tank is, being filled. From the present description and drawings, it will be appreciated that the tube structure will not be required to support all of the weight of the interior water if the water pressure is simultaneously applied to the exterior of the tube. This can be accomplished by filling the tube and the tank simultaneously. Water ingress tube 80 provides for the supply of water or other suitable liquid while egress tube 81 allows air and/or other fluids to flow out of the tube. Ingress tube 80 and egress tube 81 thus allow the tube to be filled while tank 100 is being filled. Tubes 80, 81 also allow the fluid level in the tube to be monitored and for the tube 40 to be pressurized or depressurized as desired, if the structure of the tube otherwise permits pressurization and or depressurization. The tubes are preferably filled until water flows smoothly out of egress tube 81. Additionally, after some period of use, the level of water in the tube should be checked since the tube may move during use and unintended air pockets which were not totally filled during initial filling may have been dislodged. As noted below, according to this embodiment of the present invention, care is taken to minimize the likelihood of unintended air pockets within the tubular structure.

Figure 3:
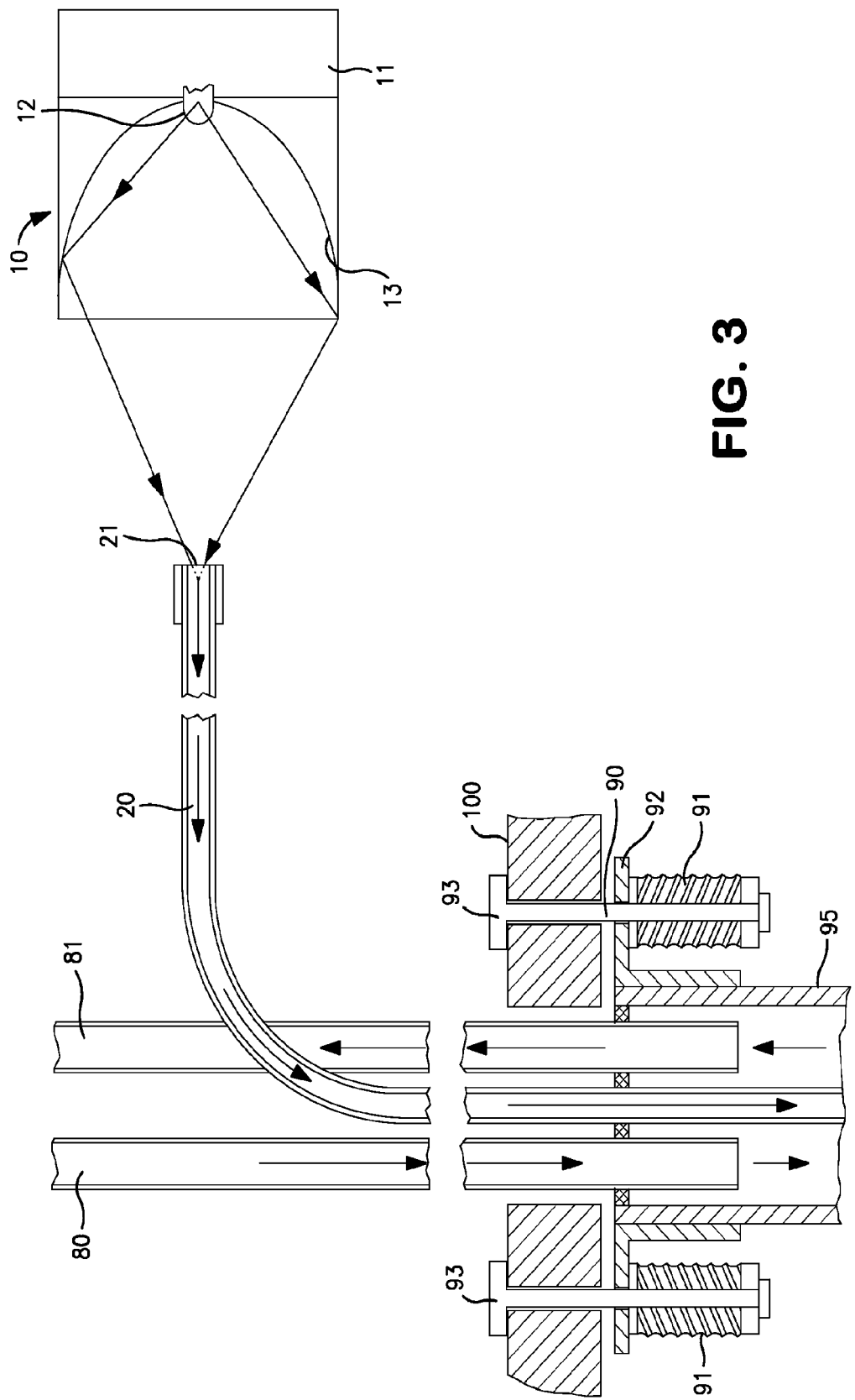
FIG. 3 is a cross-sectional view of portions of the top of the illumination device shown in FIG. 2.

FIGS. 2 and 3 shows a pair of hangers 93, shock absorbing springs 91 and a collar flange 92 which connect an upper support housing, e.g. a steel tubular sleeve, to the top of the tank 100. Upper support 95 extends downwardly to approximately the distal end 22 of fiber optic cable 20 and is secured to light injector housing 30.

Figure 4:
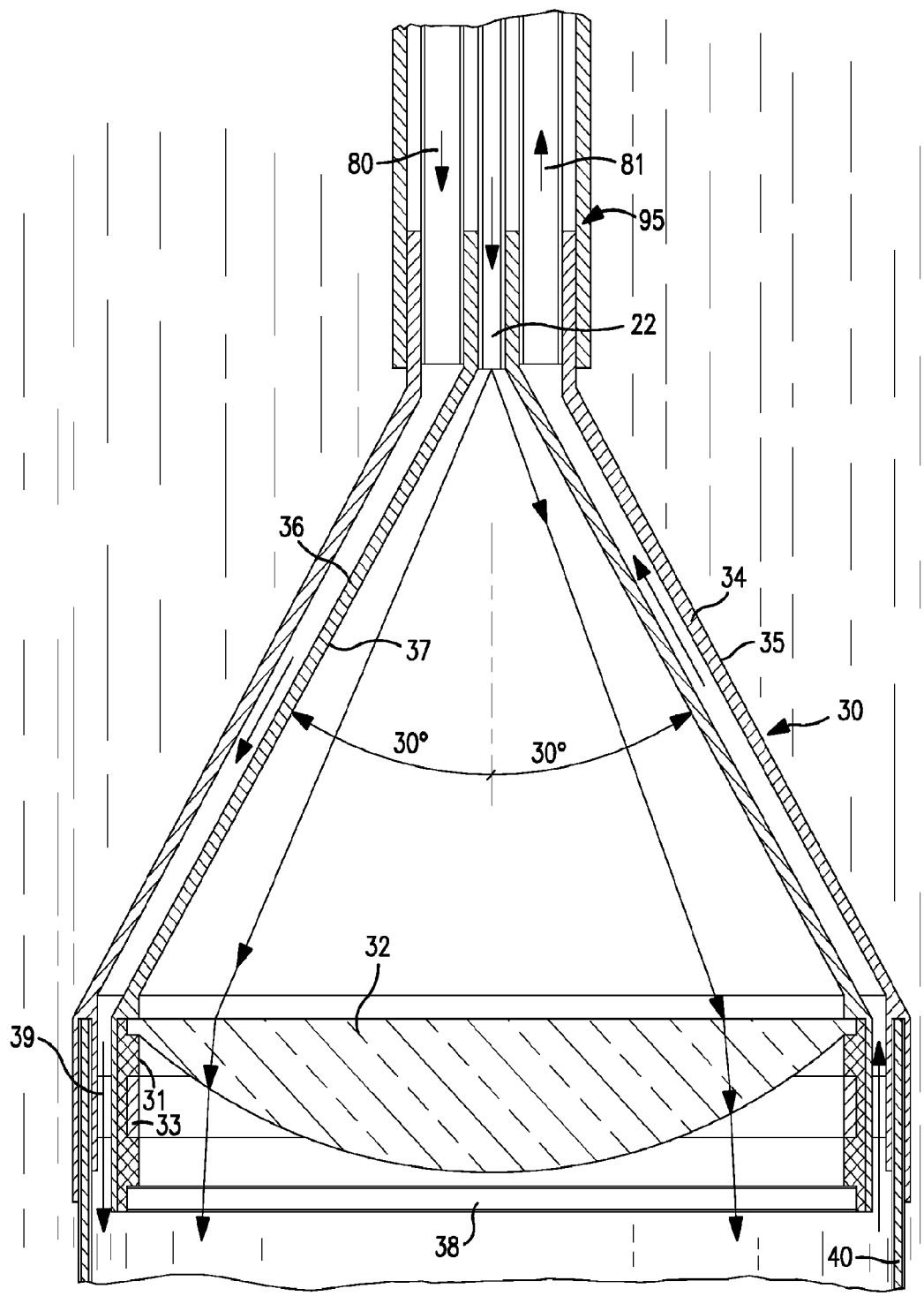
FIG. 4 is a close up of the upper portion of the light tube shown in FIG. 2.

As best illustrated in FIG. 4, light exiting the distal end 22 of the fiber optic cable 20 is directed through an optical lens 32 and thereafter into the tube 40 in this illustrated embodiment of the present invention. Light injector housing 30 of this embodiment comprises an outer housing 34 and an inner housing 36. A space is provided between outer shell 34 and inner shell 36 to allow the ingress and egress of water, air and other fluids as indicated by the arrows in FIG. 4. The interior surface 37 of inner housing 36 may be provided with a reflective coating to better direct light downwardly into the tube 40. The external surface 35 of outer housing 34 is preferably provided with a Teflon® other nonstick coating in order to minimize adherence of the algae or other organic or inorganic material in the water environment. According to this embodiment of the present invention, the space between the distal end 22 of fiber optic cable 20 and the top of optical lens 32 is preferably air but could also be water, e.g. distilled water. In order to seal this space, a gasket 31 is positioned below optical lens 32 to secure optical lens 32 to inner shell 36. Illustrated lens 32 is a planar convex lens which substantially collimates the light which strikes the top of lens 32 at an angle of incidence no greater than about 30° to provide a substantially collimated beam of light to tube 40. As used herein, the term "substantially collimated" is used to indicate that at least 90% of the light is entering the tube is at an angle of less than 10° to the longitudinal axis.

A ring 33, preferably formed of a rigid material allows screws (not shown) or other fasteners to be used to secure gasket 31 to inner housing 36. Sealant may also be used. In the embodiment of the present invention shown in FIG. 4, the lower portion of inner housing 36 is generally vertical and spaced from the similarly shaped inner walls of outer housing 34. Spacers 39 are placed intermittently around the circumference of the illumination device and also receive fasteners for securing the outer housing 34 and the upper portion of tube 40 to the lower portion of inner housing 36.

A flat glass disc 38 or optionally a lens is preferably positioned below optical lens 32 in order to provide an additional seal. If an air pocket is provided in the light injector housing 30, added buoyancy is provided to the illuminator, particularly to the upper portion of the illuminator.

Figure 5:
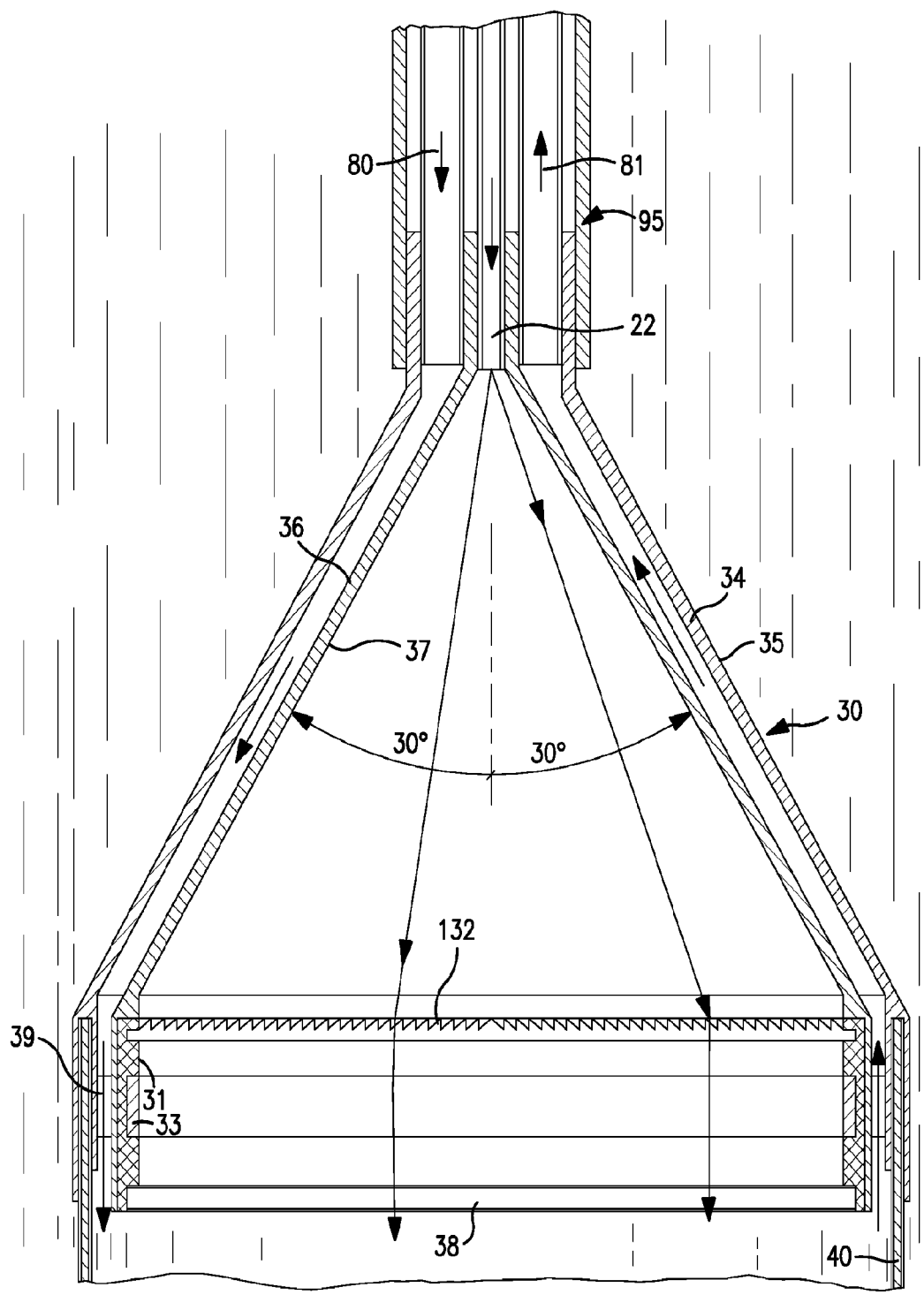
FIG. 5 is the same view as FIG. 4, but showing an alternative embodiment of the present invention.

FIG. 5 shows an alternative embodiment of light injector housing and is similar to the view of FIG. 4 with the exception of the type of lens utilized. In the embodiment shown in FIG. 5, a fresnel lens 132 replace the planar convex optical lens 32 shown in FIGS. 2 and 4. Alternatively, a bi-convex optical lens may be utilized. In this embodiment, a liquid is not utilized in the space between the distal end 22 fiber optic cable 20 and Fresnel lens 132. A liquid, such as water, would interfere with the functioning of the Fresnel lens.

Figure 6:
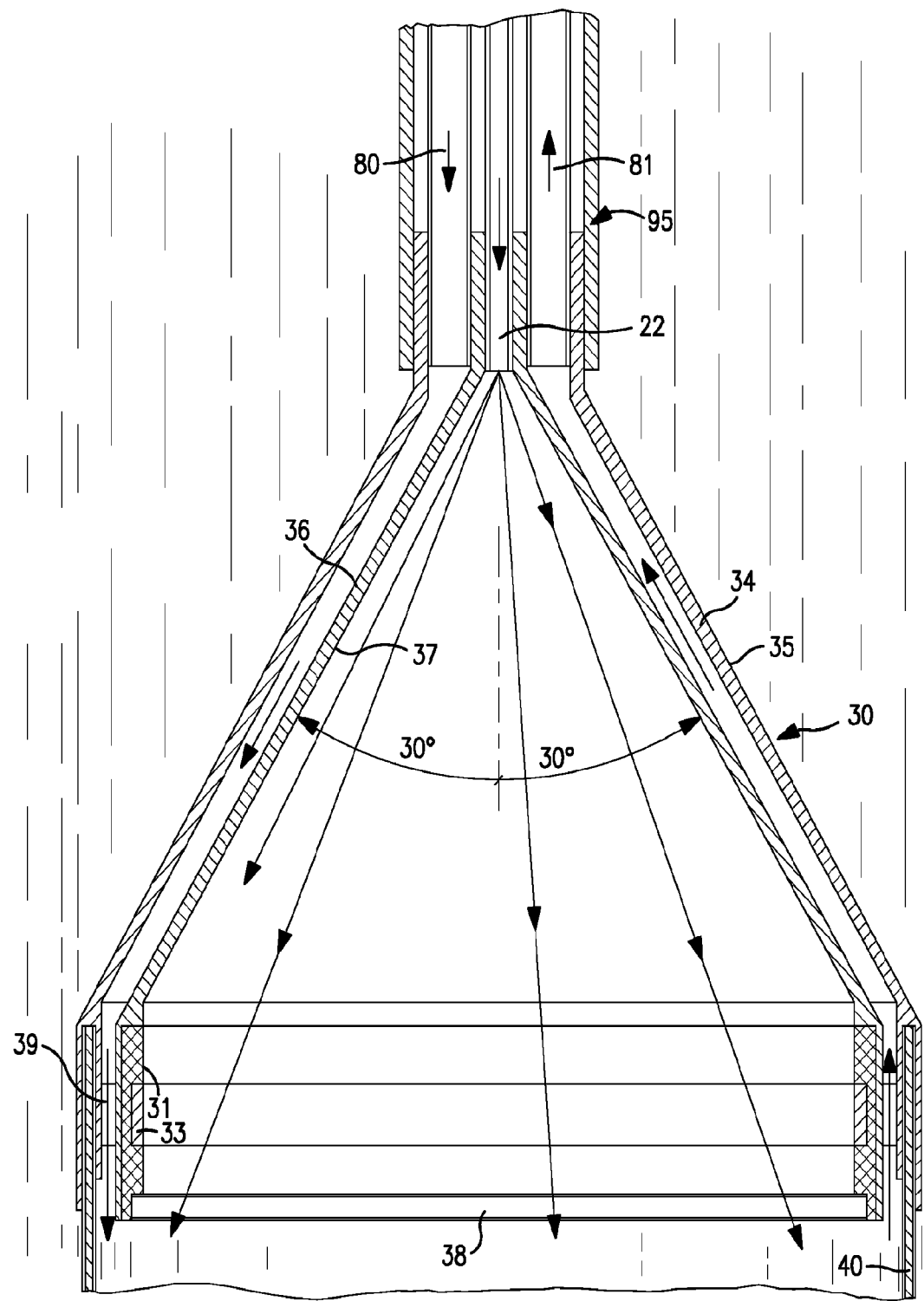
FIG. 6 is the same view as FIG. 4, but showing a third embodiment of the present invention.

FIG. 6 shows a third embodiment of the light injector housing. According to the embodiment of FIG. 6, a lens is not utilized. Some commercially available fiber optic cables emit light at an angle of about 30 degrees from the axis of the fiber optic cable. As described below, certain applications of the present invention will not require and/or will not benefit from light which is collimated by a lens such as those shown in FIGS. 4 and 5. Therefore, some embodiments will not utilize a lens in the light injector housing.

Figure 7:
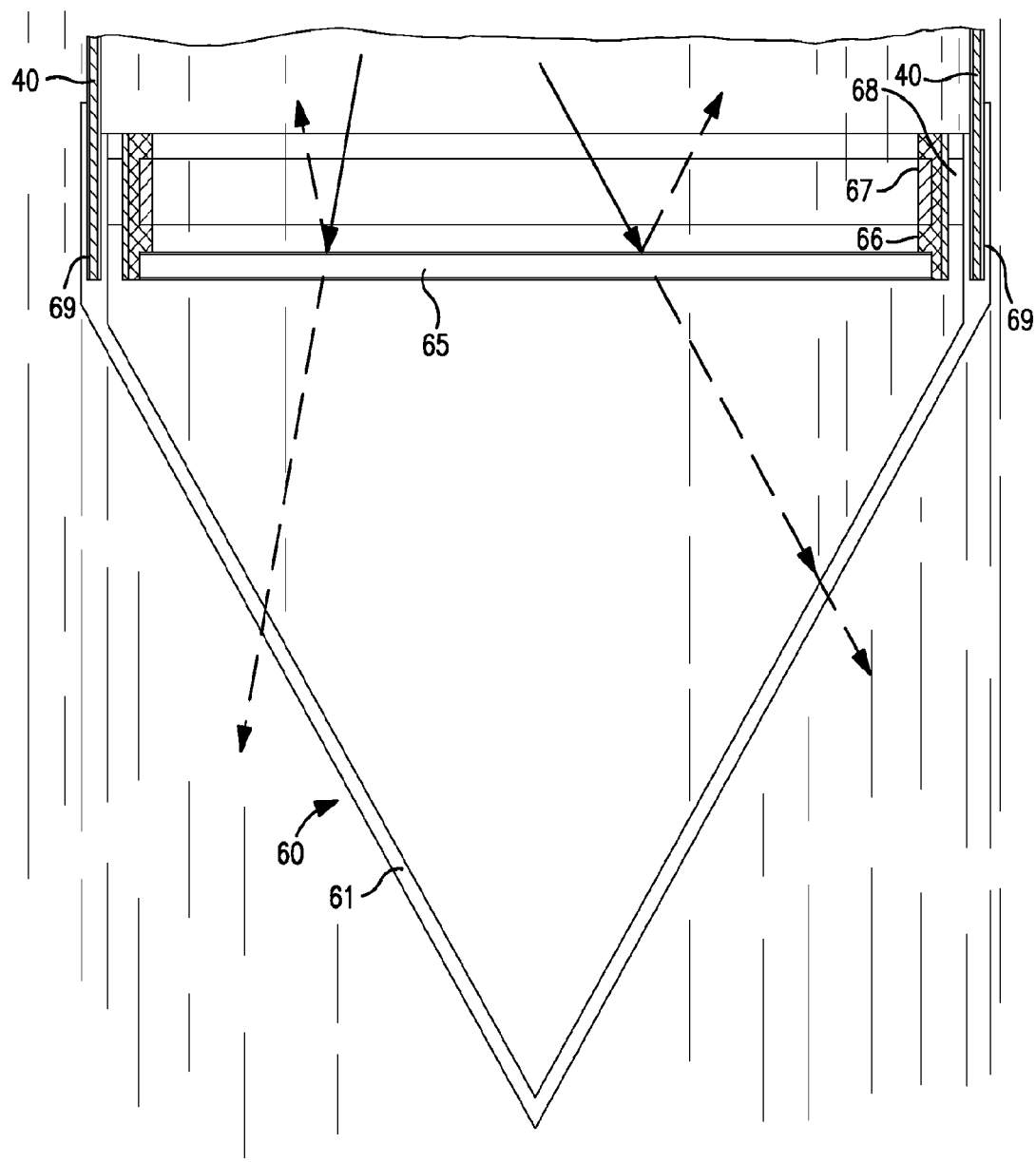
FIG. 7 is an enlarged view of the bottom portion of the illumination device shown in FIG. 2.

FIG. 7 shows an enlarged view of the bottom portion of the illumination device shown in FIG. 2 wherein the bottom of tube 40 is provided with an end cap 60 comprising a diffusing, preferably translucent and most preferably transparent, conical lower portion 61 which allows light to pass into the water environment. A mirror 65 is supported by a gasket 66 which is held in place by fasteners (not shown) which pass through support ring 67, gasket 66, spacers 68, tube 40 and the upper, substantially vertical portion 69 of end cap 60. Spacers 68 positioned between mirror support 66 and the upper, interior surface of end cap 60 are not continuous around the circumference of the tube and therefore provide gaps for fluid to flow between end cap 60 and mirror support 66. Thus water, other suitable liquids, air or other gases are permitted to flow relatively freely into and out of the space below mirror 65 inside end cap 61. In this illustrated embodiment, mirror 65 is partially reflective thereby reflecting only a percentage, e.g. 20%, of the light back up into the tube and allowing substantially the remainder of the light to be transmitted downwardly through the conical portion 61 of end cap 60. As an alternative to a partially reflective mirror, mirror 65 could simply be provided with a noncontinuous structure which covers only a portion of the area defined by the bottom of tube 40.

If desired, some or all of the structure used at the bottom of the tube, such as for the mirror support 66, support ring 67, and/or spacer 68 can be formed of relatively heavy materials in order to assist in weighing the bottom of the illumination device down. The water environment may not be stable and may be somewhat turbulent in order to facilitate mixture of gases, algae and other constituent components, and or to accommodate a large flow of $CO_2$. Therefore, extra weight near the bottom of the illumination device will tend to keep the device more vertical in the tank. Additionally, end cap 60 is preferably coated with or made from a nonstick material, such as Teflon® FEP, in order to minimize adhesion by dirt, algae, or other matter which would block the desired transmission of light.

The following is a description of various embodiments of tubular structures which are useful with the illumination devices and illumination systems of the present invention. While each of these embodiments is illustrated in the form of substantially circular cylinders, other shapes and configurations may be utilized. Circular cylinders are believed to be preferred because they have a minimal surface area and are more readily made such that they are structurally sound.

Each of the illustrated illumination devices comprises a body portion, preferably in the form of a circular cylinder, which emits light over substantially its entire length. In certain applications, for example when utilized in a tank having a depth of about 20 meters, it may be preferable to form tubes in segments for ease of manufacture and shipping. It may also be desirable in certain applications to utilize segmented tubes wherein different segments have different characteristics in order to provide different amounts of illumination at different positions outside the tube. The tubes 40 are not necessarily uniform along their entire length. For example, it may be desirable to permit more light to emanate from an upper portion of the tube 40 where the concentration of algae in the water may be greater than at a lower region of the tank where the algae concentration may be lower. Each of the illustrated tubular light tubes is filled with a column of water, e.g. distilled water, or another fluid which readily transmits light. For most applications it is currently believed that a clear liquid is preferred, however, it may be desirable in certain applications to use fluids which provide advantageous effects to the wavelength of the light emitted from the illumination device.

Figure 8:
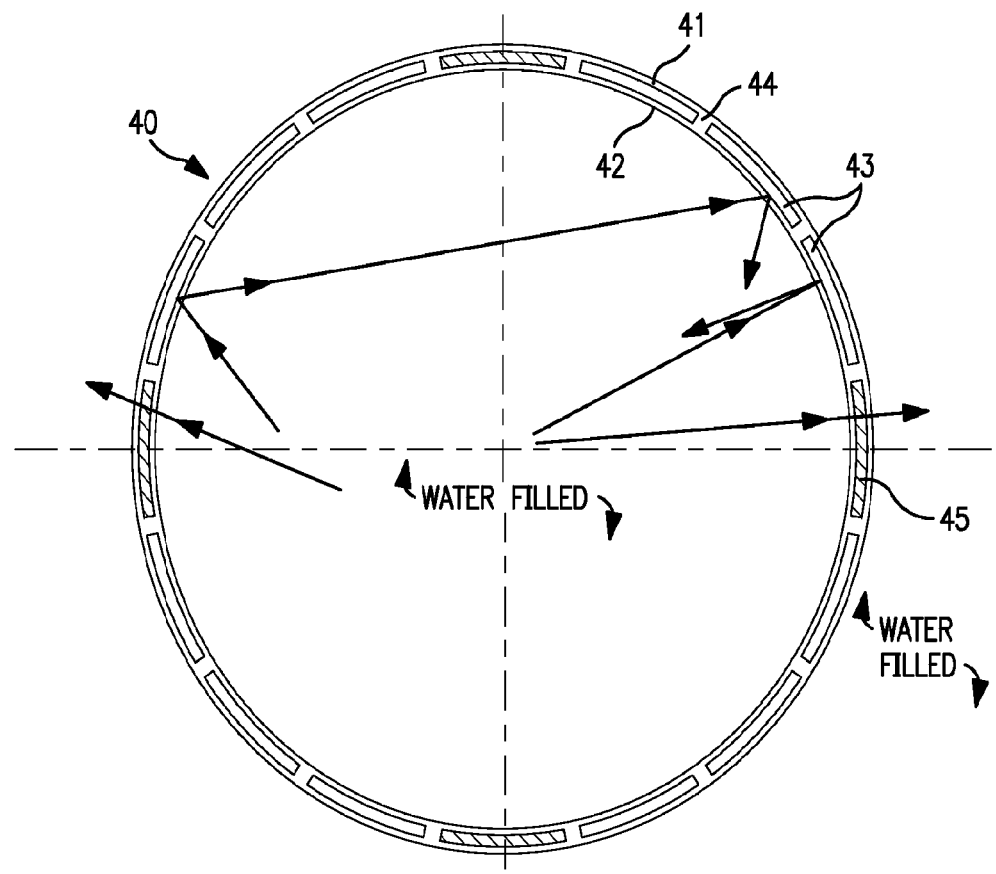
FIGS. 8 and 9 illustrate a tube structure which can be used with the illumination device of FIG. 2.
Figure 9:
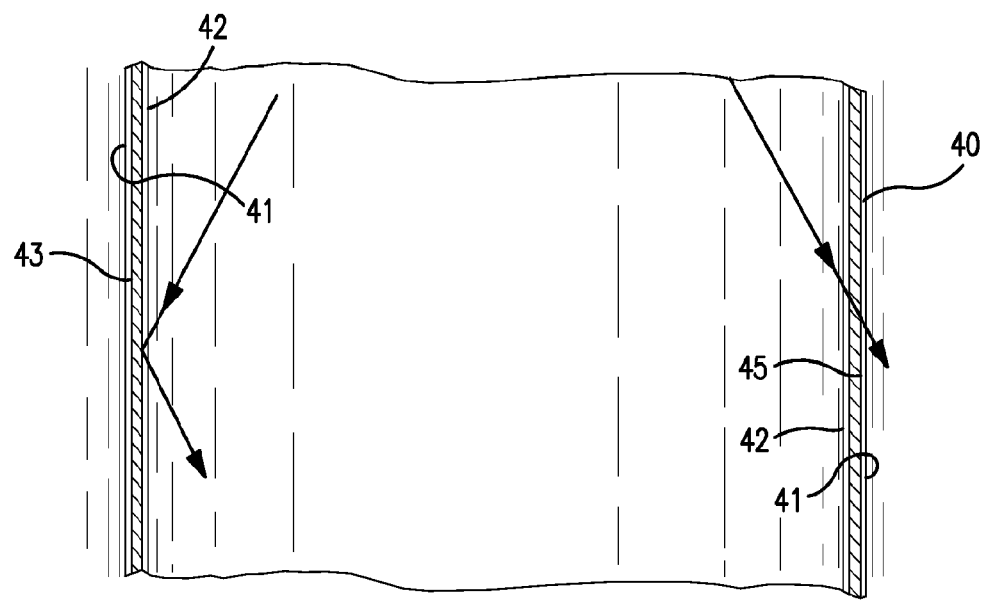

FIGS. 8 and 9 are cross-sectional top and side views, respectively, of a first embodiment of a tube of the present invention. According to this illustrated embodiment, tube 40 is in the form of a twin walled tube comprising an outer wall 41, an inner wall 42 and a plurality of ribs 44. In the illustrated embodiment, tube 40 is formed as an integrally extruded tube. Hollow portions 43 of the tube 40 between spacers 44 can be left hollow or can receive inserts 45. The inserts can be formed of the same material as the inner wall 42 and outer wall 41. One preferred material is Teflon® FEP, made by DuPont which is a fluorinated ethylene propylene. Other inserts can be liquid, e.g. water, which has an index of refraction close to FEP.

Depending upon the material used to form the tube, light striking interfaces, e.g. the interface between the inner wall 42 and the hollow cavity 43, at an angle of incidence below a predetermined critical angle will be internally reflected back into the tube interior at locations where there is no insert 45 in a hollow cavity 43. However, where an insert 45 is positioned within the hollow spaces, light will pass through the sidewall of tube 40 to the exterior water environment.

The hollow central tubes shown in FIGS. 8 and 9 are filled with water, preferably distilled water, and are positioned in a water environment. Water has an index refraction of about 1.33 while Teflon® FEP made by DuPont has a very close index of refraction of about 1.35. The index of refraction of the Teflon® FEP is close to that of water when compared with that of air which has an index of refraction of about 1.0 and common, transparent polycarbonate which has an index of refraction of about 1.58. Common glass has an index of refraction of about 1.5, while borosilicate has an index of refraction of about 1.47 and that of Crown glass (pure) can be 1.54. In light of the similar indices of refraction of water and FEP, light traveling through a portion of the illustrated tube which contacts the FEP insert, i.e. not a hollow cavity, will be less likely to be internally reflected.

FIG. 9 generally illustrates a beam of light being internally reflected on the left interior side of tube 40 which does not have an insert in a hollow portion 43, while a beam of light impinging at the same angle on the right side of the tube passes through the sidewall of the tube in an area corresponding to an insert 45.

Figure 10:
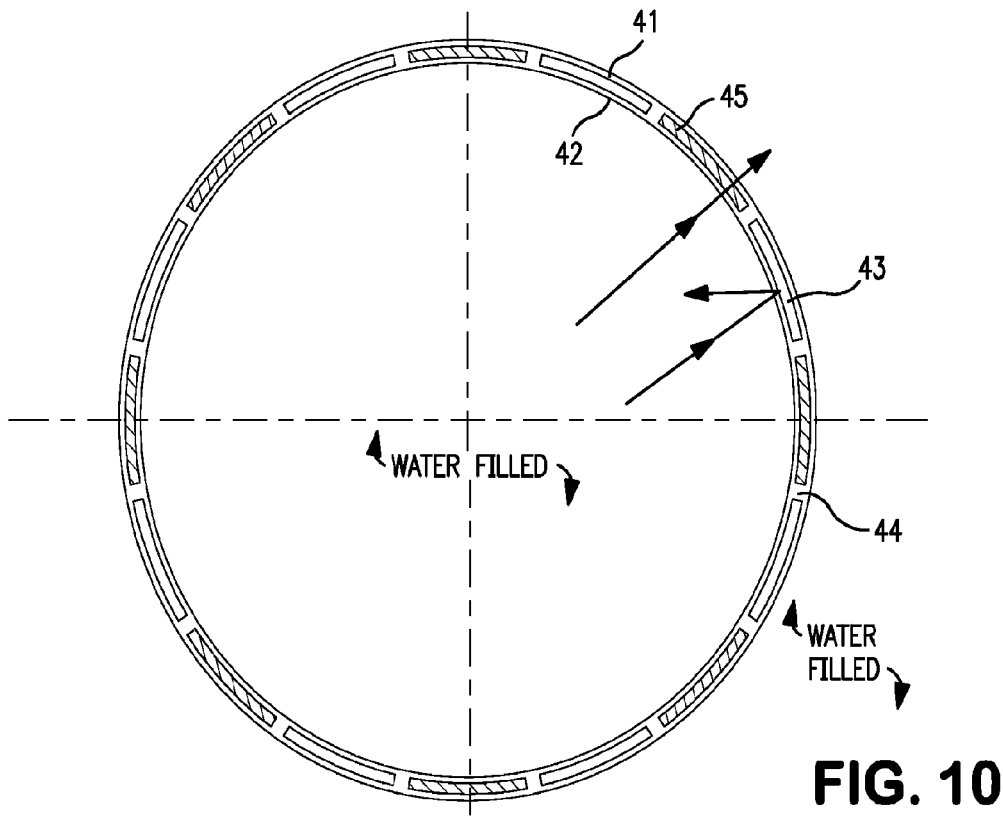
FIGS. 10 and 11 illustrate different configurations of the tube shown in FIG. 8.
Figure 11:
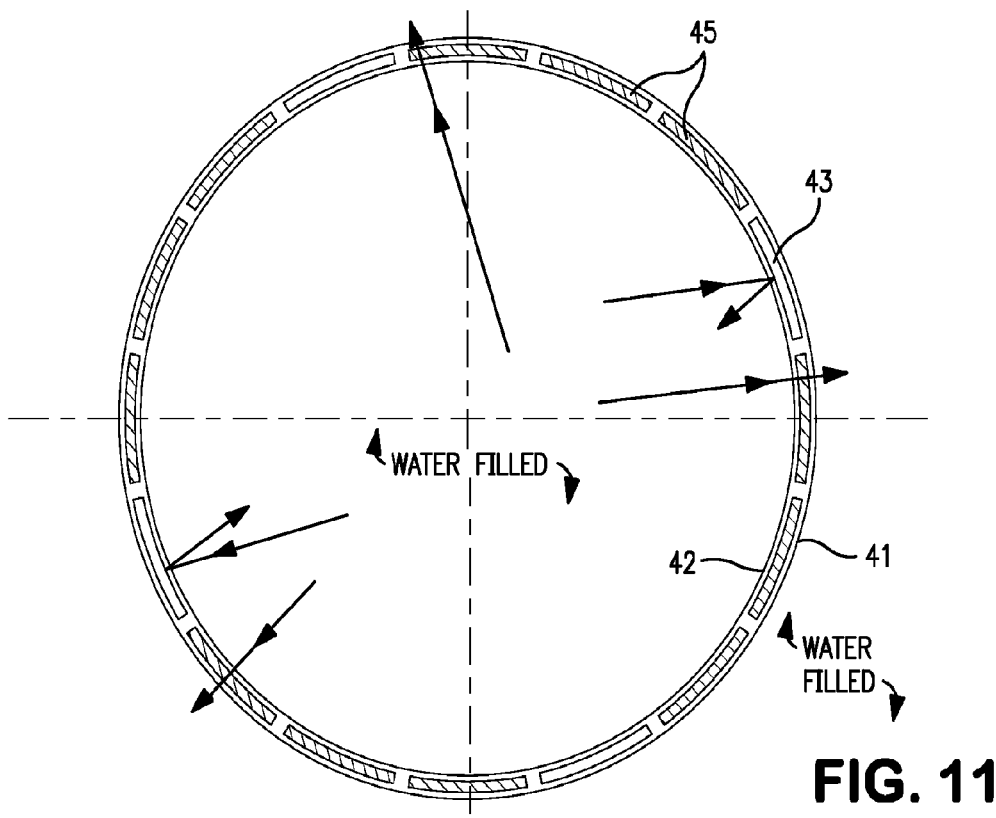

FIGS. 10 and 11 illustrate either an alternative embodiment of the present invention or a different segment of tubing used as part of a segmented tube, but wherein more of the hollow portions 43 have been filled with inserts 45. Compared to the section of tube illustrated in FIG. 8, from the present description, it will be understood that light is permitted to pass through more areas of tube sidewalls of tube 40 in the tube segments illustrated in FIGS. 10 and 11 which are filled with more inserts 45.

Since most light which travels up and down the tube will preferably be traveling at an angle of less than 30° to the longitudinal axis of the tube, the use of inserts in this embodiment will generally prescribe where light is transmitted from the tube and where light is internally reflected.

Figure 12:
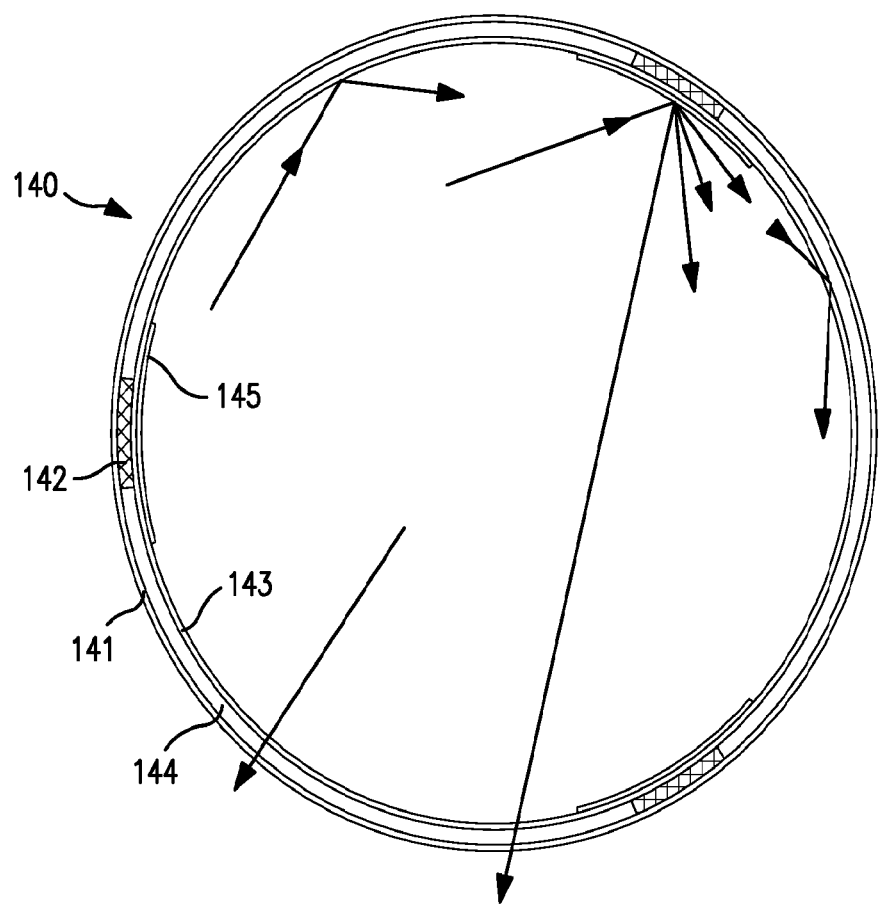
FIGS. 12 and 13 are top and side cross-sectional views, respectively, of a tube of an alternative embodiment of the present invention which can be used with the illumination device of FIG. 2.
Figure 13:
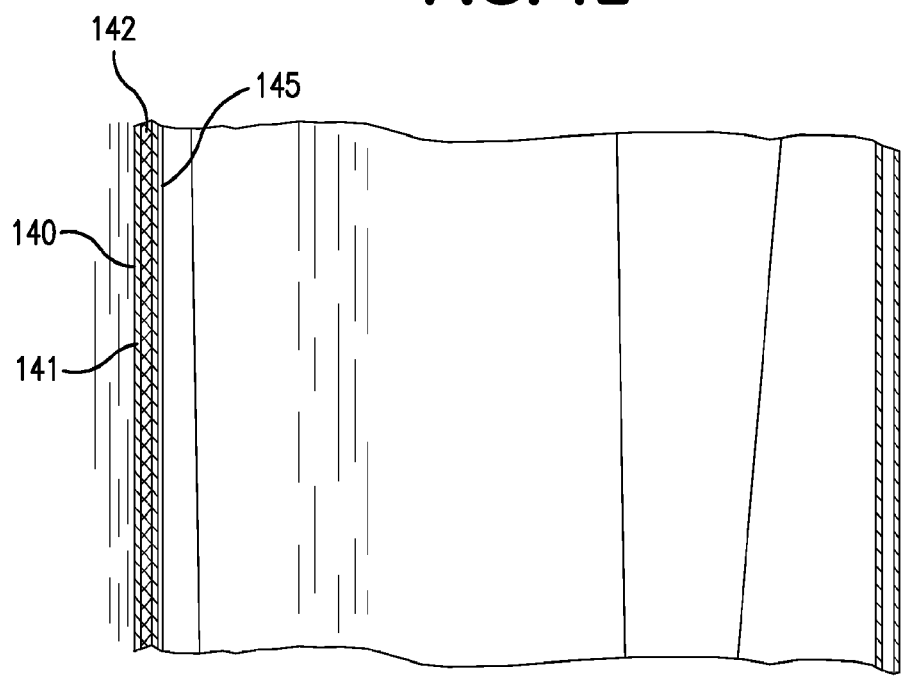

FIGS. 12 and 13 illustrate another embodiment of the present invention. In this embodiment, tube 140 comprises an outer wall 141 preferably formed of a nonstick material such as Teflon® FEP. Outer wall 141 can also be formed of material such as polycarbonate, PVC, acrylic or glass. A plurality of spacers 142, preferably formed of a plastic material in an arcuate shape, separate an inner wall 143 from outer wall 141. Spacers can be formed of other materials such as metals, e.g. aluminum, wood or ceramics. Inner wall 143 can be formed of materials such as those described above for outer wall 141 and is, most preferably, formed of the same material as outer wall 141. Spacers 142 therefore define a space 144 between outer wall 141 and inner wall 143. Additionally, an extractor 145 which is preferably an opaque, textured material is positioned inside inner tube 143. For example, one preferred extractor is made by the 3M Company of St. Paul, Minn. and is a matte white Scotchcal® which is preferably adhered to a textured substrate. According to this embodiment of the present invention, light traveling down tube 140 which strikes an extractor 145 will be scattered and will thereby strike another portion of interior tube 143 at an angle of incidence greater than the critical angle of refraction and will therefore pass through the tube to the exterior environment. Extractors 145 can be tapered as desired.

Figure 14:
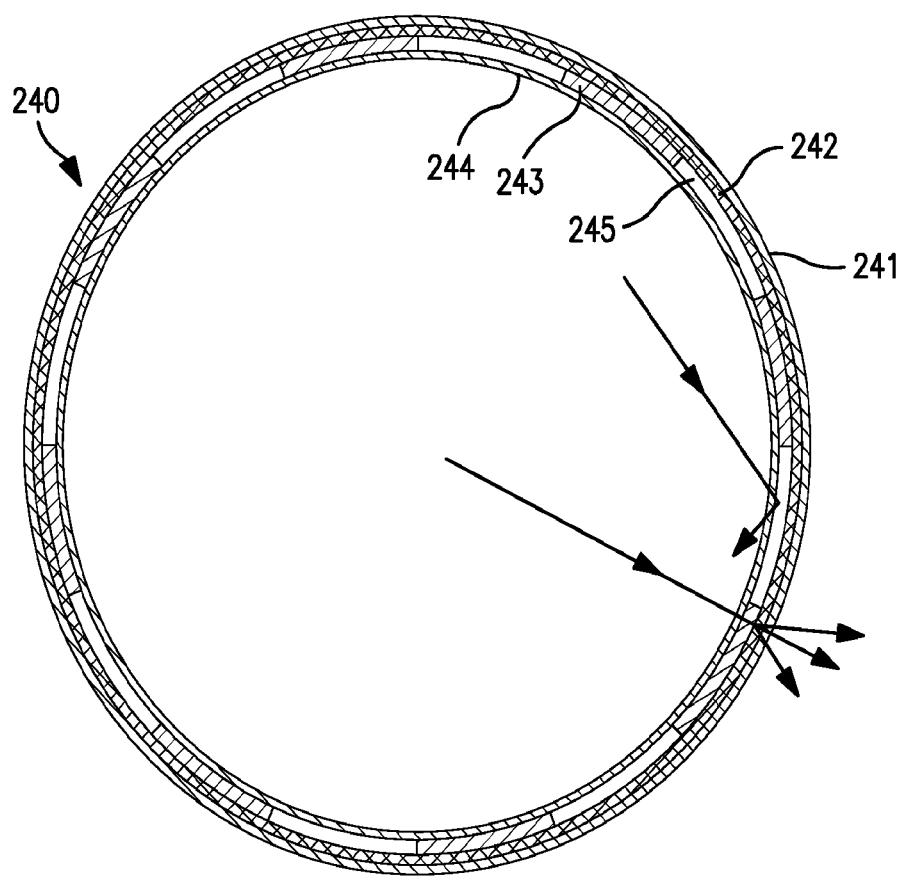
FIGS. 14 and 15 are top and side cross-sectional views, respectively, of a third tube which can be used with the illumination device shown in FIG. 2.
Figure 15:
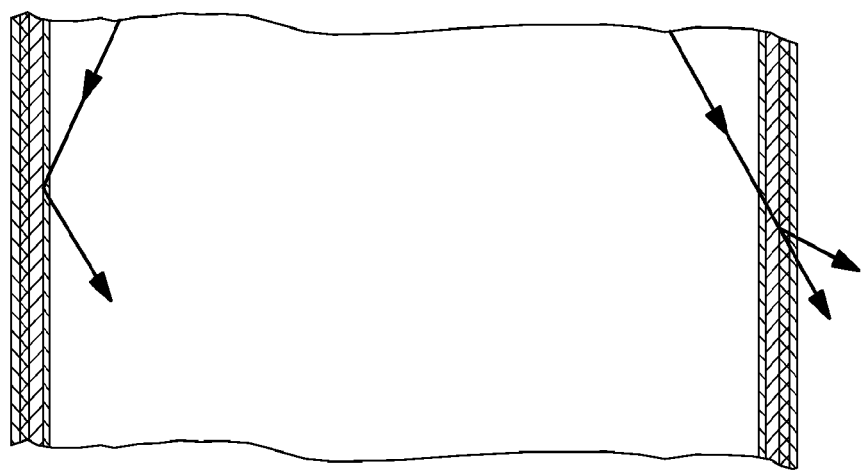

FIGS. 14 and 15 illustrate a further embodiment of the present invention wherein tube 240 comprises an outer tube 241 and a spaced inner tube 244 which can both be formed of the same material as outer tube 141 of FIG. 12. Positioned interiorly of outer tube 241 is a diffusing film 242 which can be formed of, for example, one or more of polycarbonate velvet, matte or suede textured films. Diffusing film 242 is preferably continuous and scatters light. Positioned interiorly of the diffusing film 242 and outside of inner tube 244 is at least one and preferably a plurality of intermediary film spacers 243. Spacers 243 can be formed of a film, e.g. a transparent polished/polished polycarbonate film, or a rigid, clear, arcuate segment, e.g. a polycarbonate. Air gaps 245 exist between spacers 243. According to this embodiment of the present invention, when light traveling down tube 240 strikes a portion of the interior tube 244 corresponding to both an intermediary film spacer 243 and the diffusing film 242, some of the light will be directed out of the tube. Specifically, most of the light which is not internally reflected by the interior surface of the inner tube will be directed out of the tube in these portions of the tube.

Figure 16:
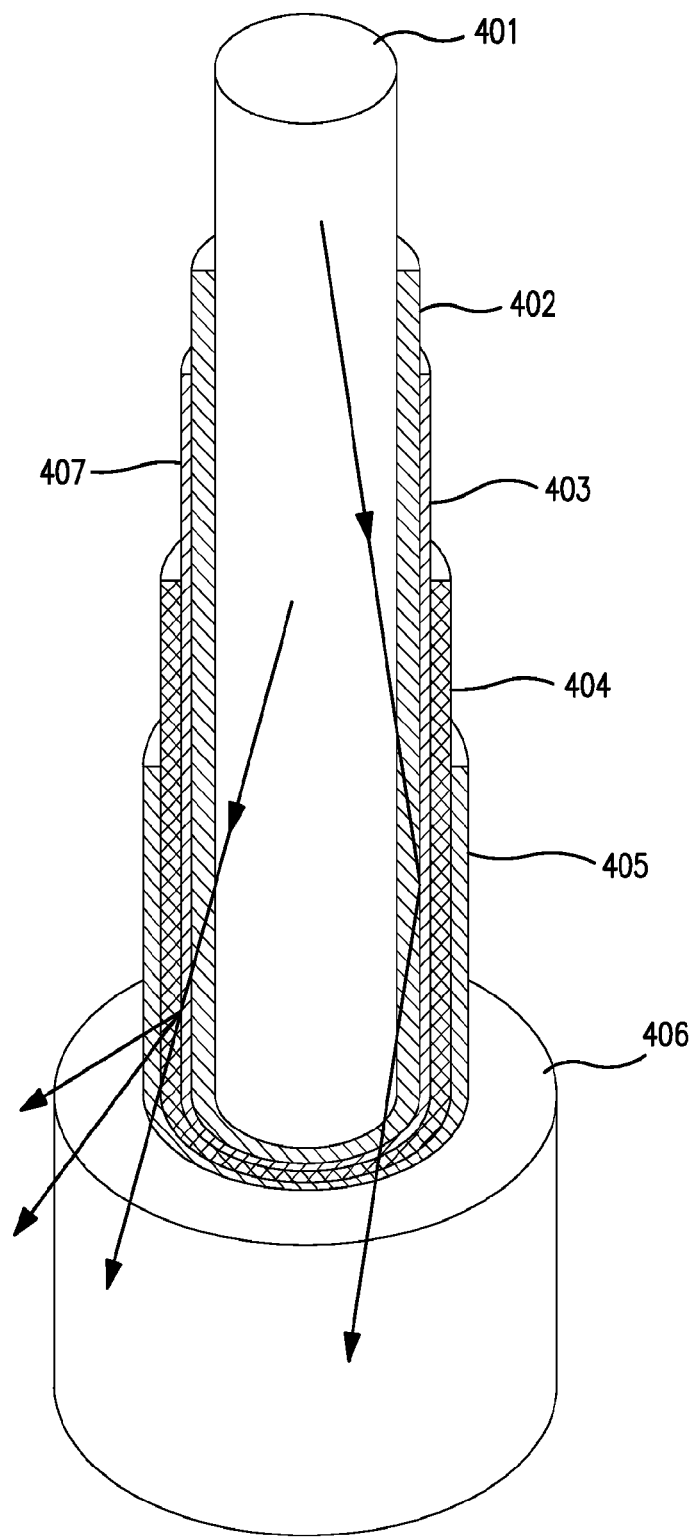
FIG. 16 is a schematic illustration of the interfaces between materials used with one embodiment of the present invention.

FIG. 16 is a diagrammatic illustration of how light passes through components of the present invention. According to this illustration, 401 illustrates a column of liquid, for example distilled water. Column 402 is an FEP tube. Column 403 represents a space, i.e. an air gap. Column 404 represents a diffusing film and column 405 represents an exterior tube formed of FEP. Column 406 represents a water environment outside of exterior tube 405. Material 407 represents a spacer. The space(s) between spacers 407 define the air gaps 403. As indicated by the downwardly directed arrow on the right in FIG. 16, light traveling down the interior column of water 401 will pass through the interior tube 402 of FEP since water and FEP have a very close index of refraction. However, when the light hits the interface between interior tube 402 and air space 403, since the light would be passing from a medium having a higher index of refraction to a medium having a lower index of refraction (air), light which is incident at an angle below the critical angle is internally reflected. The downward arrow on the left of this Figure represents light which passes through the interior tube 402 to the spacer 407 which has a higher index of retraction than interior tube 402. This light continues outwardly to diffusing layer 404 where it is then scattered in different directions including directions which cause it to travel through exterior tube 405 and into the water environment 406.

The light supplied to the light distributing tubes of the embodiments shown in FIGS. 8-18 is not necessarily substantially collimated, however for light distributing tubes having large aspect ratios, e.g. a 60 foot long tube having a diameter of 6 inches, it may be desirable to supply a substantially collimated beam of light.

Figure 17:
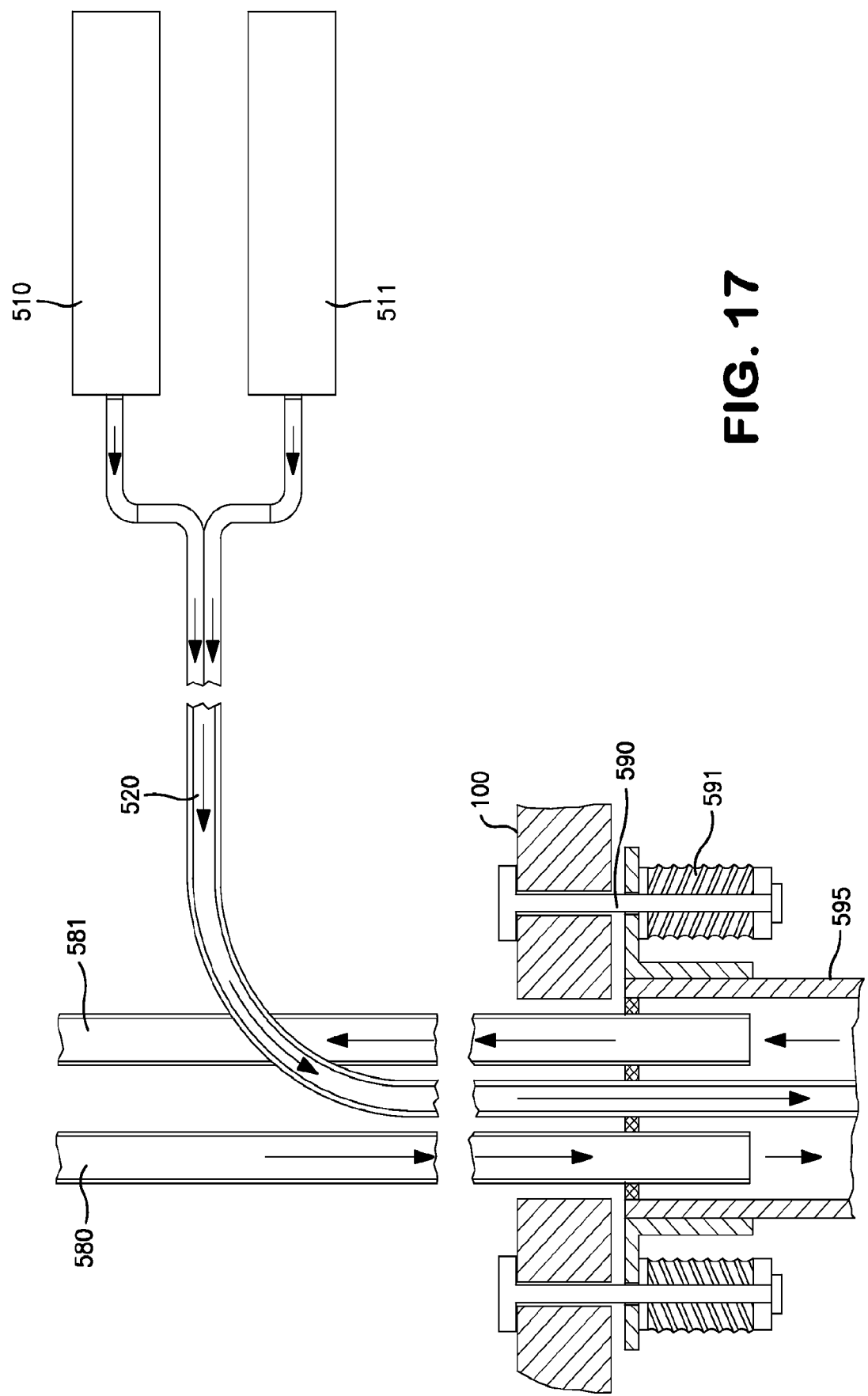
FIG. 17 is a cross-sectional view of portions of the top of an alternative embodiment of an illumination device of the present invention.

FIG. 17 illustrates one embodiment of the present invention which is useful with a liquid filled light distribution tube of the type disclosed in Applicants' co-pending U.S. provisional patent application Ser. No. 61/215,368 filed on May 4, 2009. According to this embodiment of the present invention, light from a first laser light source 510 and a second laser light source 511 are transmitted, via a fiber optic light carrier, to a light distribution tube. Laser light sources 510 and 511 can be used simultaneously, sequentially and/or alternatively to provide light of different wavelengths to the light distribution tubes.

Figure 18:
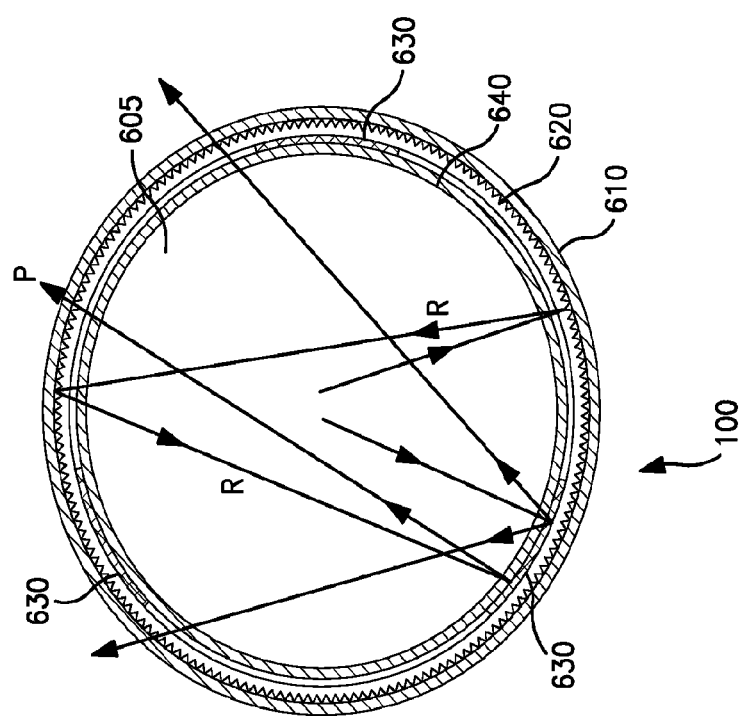
FIGS. 18 and 19 are top and side cross-sectional views, respectively, of a light distribution tube of an alternative embodiment of the present invention.
Figure 19:
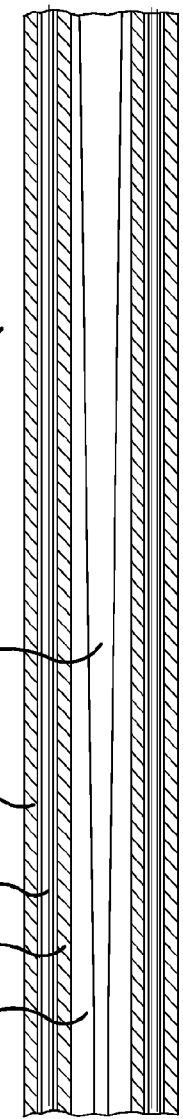

FIGS. 18 and 19 illustrate an alternative embodiment of the present invention wherein a liquid filled light distribution tube comprises a tube within a tube. According to this embodiment of the present invention, the light distribution tube whose interior is substantially filled with a liquid 605 as describe above comprises exterior wall 610, an optical light film 620, a plurality of extractors 630 and an inner wall 640. This embodiment of the present invention does not depend upon a collimated source of light in order to efficiently transmit light along substantially its entire length but preferably has an angle of divergence not greater than about 28°. Light directed into the tube will be internally reflected by the optical light film if it strikes the optical light film at an angle of incidence of less than about 28°. The extractors 630 have an effect similar to the extractors described above wherein light striking extractor 630 will be reflected toward sides of tube 600 at angles greater than the maximum angle of internal reflection as shown by arrows P and will pass through the optical light film 620 and outer walls 610. Light striking optical light film 220 at lesser angles of incidence will be internally reflected as shown by arrows R until reaching a mirror end cap (not shown) or subsequently striking extractor 230.

Figure 21:
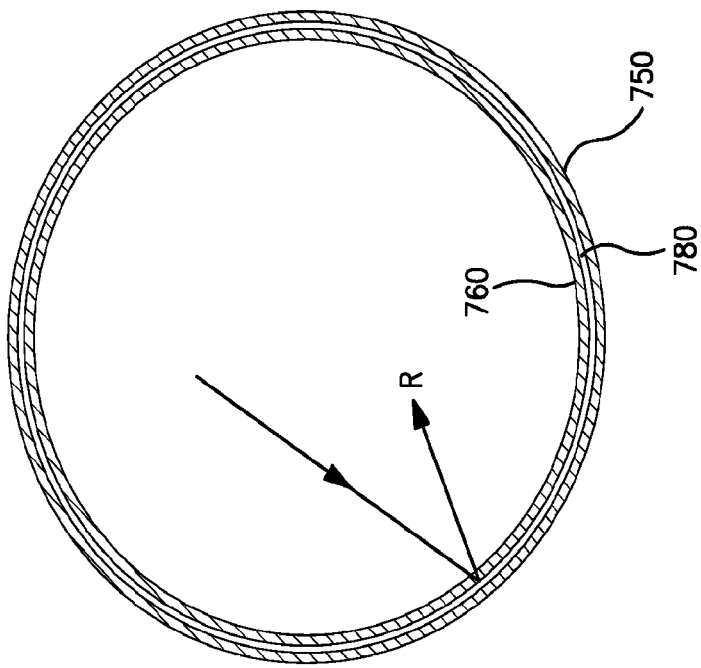
FIGS. 20 and 21 are top and side cross-sectional views, respectively, of a light distribution tube of an alternative embodiment of the present invention.
Figure 20:
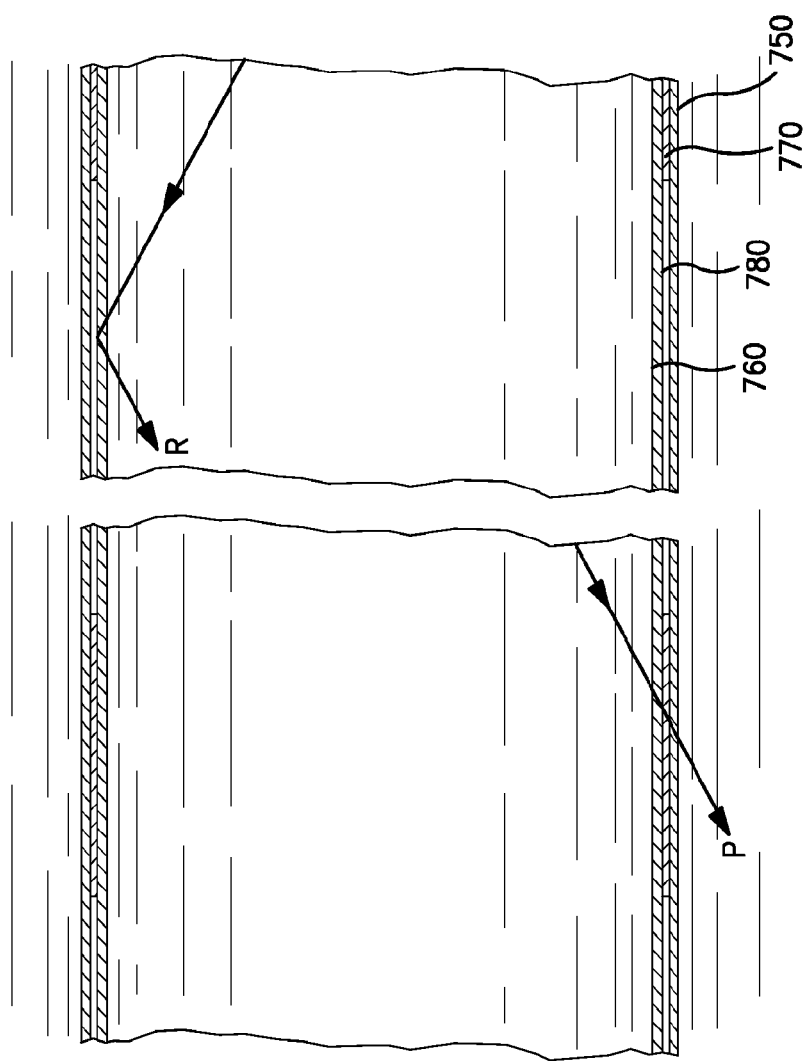

FIGS. 20 and 21 illustrate another liquid filled light distribution tube comprising an outer wall 750 formed of Teflon FEP (hereinafter "FEP"), an inner wall 760 formed of FEP and a plurality of spacer rings 770 also formed of FEP. Rings 770 preferably extend around the entire circumference of inner wall 760. The spaces 780 between the spacer rings 770 are preferably filled with air. The interior of the tube, i.e. interior of inner wall 760, is filled with a liquid, e.g. water. Since FEP has an angle of refraction close to that of water, light striking areas of the tube which have a spacer ring 770, i.e. which are formed of three layers of FEP, will generally continue on its path out of the tube. However, light striking the interface between inner tube 760 formed of FEP and the air between the spacer rings 770 will be internally reflected since the index of refraction of air is substantially less than that of FEP. Arrows R and P in FIGS. 20 and 21 indicate light being internally reflected and passing through the tube walls, respectively.

According to an alternative to the embodiment shown in FIGS. 22 and 23, the spacer rings are formed of a reflective material and the spaces between the spacer rings are filled with water. In this embodiment, the light will pass through the tube in the areas between the spacer rings and be reflected in the areas of the spacer rings.

FIGS. 22-24 illustrate a liquid filled light distribution tube of one embodiment of the present invention wherein tube 800 is substantially filled with a liquid 805, preferably a clear liquid such as water, and is provided with a light extractor 810, such as matte white Scotchcal® made by the 3M company of St. Paul, Minn., positioned on the inside of tube 800.

As best shown in FIG. 22, a fiber optic light carrier 820 is connected to a lens housing 840 by a ferrule 830. Light exiting fiber optic light carrier 820 is directed through a lens 850, such as the illustrated Fresnel lens, which substantially collimates the light for transmission down the length of tube 800. Light striking extractor 810 will be reflected toward sides of tube 800 at angles greater than the maximum angle of internal reflection as shown by arrows P and will pass through the walls of tube 800. Most of the light which does not contact the extractor 810 will either go directly to mirror end cap 860 for reflection back up the tube or will strike interior walls of tube 800 at angles less than the maximum angle of internal reflection as shown by arrows R and will be internally reflected by the walls of tube 800. Exterior tube 800 can be formed of acrylic, glass, polycarbonate, PVC and/or FEP. The indices of refraction of the liquid inside the tube and the tube wall are preferably as close as possible. Additionally, the exterior of outer wall 40 is preferably either formed of or provided with a coating which has low-friction and low-reactivity properties, as well as high light transmission. While the interior liquid is preferably water, other liquids such as mineral oil or silicone oil, or the like could also be utilized. It is also within the scope of the present invention to use light sources which are not carried by fiber optics.

The extractor 810 of the embodiment shown in FIGS. 22-24 can be replaced by a distributor of the type disclosed in U.S. Pat. No. 6,014,489 entitled LIGHT DISTRIBUTING TUBES AND METHODS OF FORMING SAME. A light distributor 1200 which is illustrated in FIG. 25 is preferably spaced a certain distance from the light input end of the tube 1210 (depending on the beam spread angle of the light beam). The illustrated distributor 1200 can include a light scattering lamination carried on a substrate formed of polycarbonate with a rough or textured surface. One suitable substrate material is sold under the trademark Lexan® Suede by the GE Company. Such a lamination is preferably tightly mated to the rough or textured surface of the substrate and is a thick, white matte film such as Scotchcal sold by the 3M Company. The light distributor 1200 is preferably gradually tapered over its full length, most preferably symmetrically on both edges from a narrow width toward the end of the tube into which light is injected to a width at the distal end which is close to but not greater than one half of the internal circumference of the tube.

A relatively inexpensive embodiment of a liquid-filled light distribution tube of the present invention comprises a clear PVC tube with a distributor of the type disclosed in U.S. Pat. No. 6,014,489 disposed in the tube and the tube substantially filled with a clear liquid such as water. The tube is connected to a source of substantially collimated light which is beamed into the tube parallel to the longitudinal axis of the tube. Light striking the distributor will be reflected at the inner tube wall at an angle which will cause most of that reflected light to pass through the tube wall.

The embodiments of the present invention shown in FIGS. 1-26 are liquid filled light distribution tubes designed to operate in a submerged environment such as a bioreactor used to grow organisms such as algae. These embodiments can advantageously distribute light over substantially their entire lengths while having an internal pressure and buoyancy closely compatible with their external environment.

FIGS. 27-30 illustrate a bioreactor of another embodiment of the present invention. FIGS. 27 and 28 are cross-sectional views of a continuous bioreactor wherein a plurality of liquid filled light distributing tubes 910 are positioned generally horizontally in a bioreactor tank 900. Carbon dioxide is supplied to the bottom of the reactor via supply tubes 920.

Desired additional compounds or organisms, such as algae, can also be supplied to bioreactor 900 via supply tubes 920. As algae grows and accumulates at the top of the tank 900, it is moved by a movable skimmer 930 mounted on wheels/rollers 935 and having at least one skim tab 937, into collection troughs 940 positioned on either side of the tank 900 as best illustrated in FIG. 27. Skimmer 930 is supported by a support, e.g. a monorail proximate the top of the tank. Skimmer 930 can be positioned at, above or below the surface of the liquid mixture in the tank.

Figure 29:
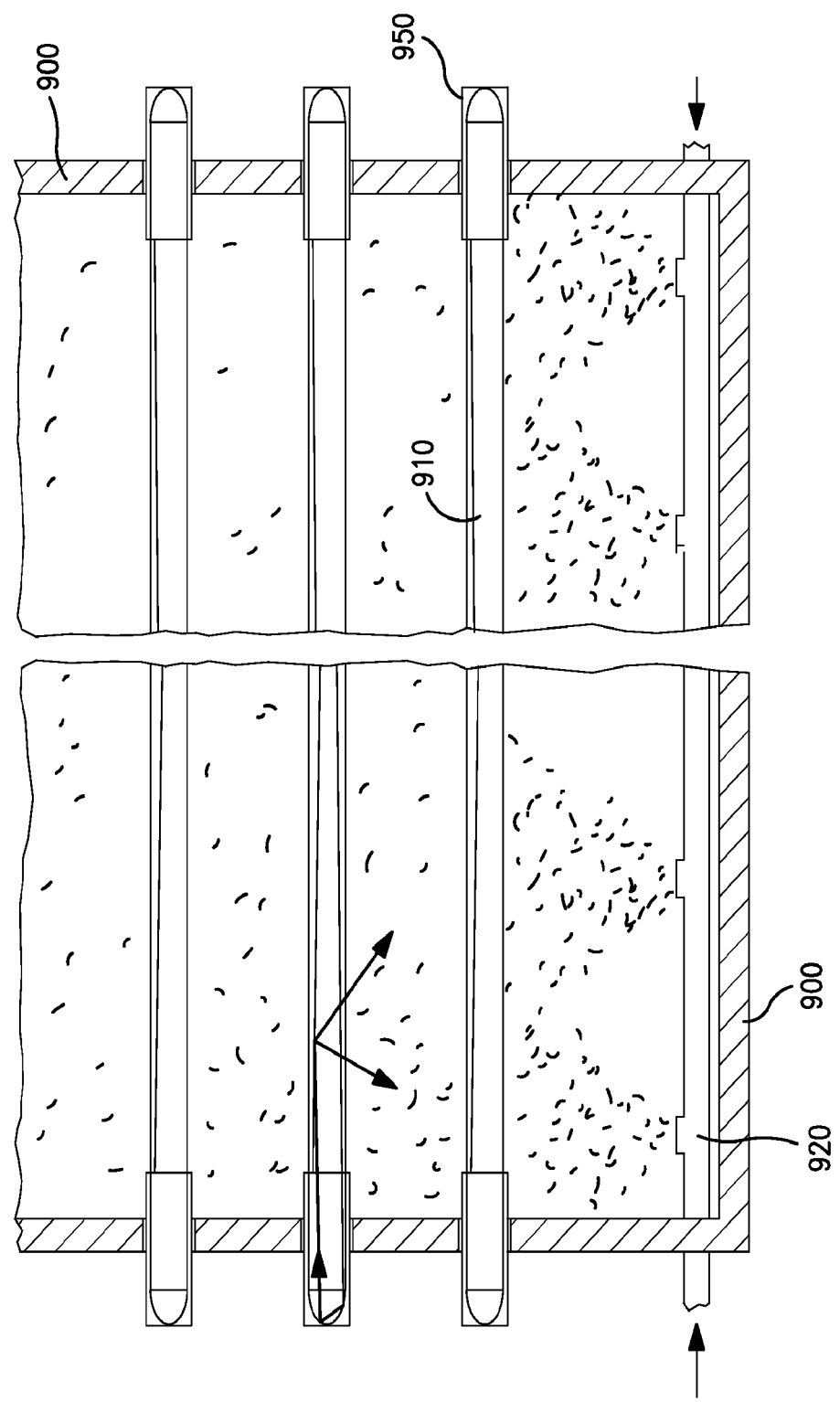
FIG. 29 is a close-up of the cross-sectional view of a portion of the bioreactor shown in FIG. 28.
Figure 30:
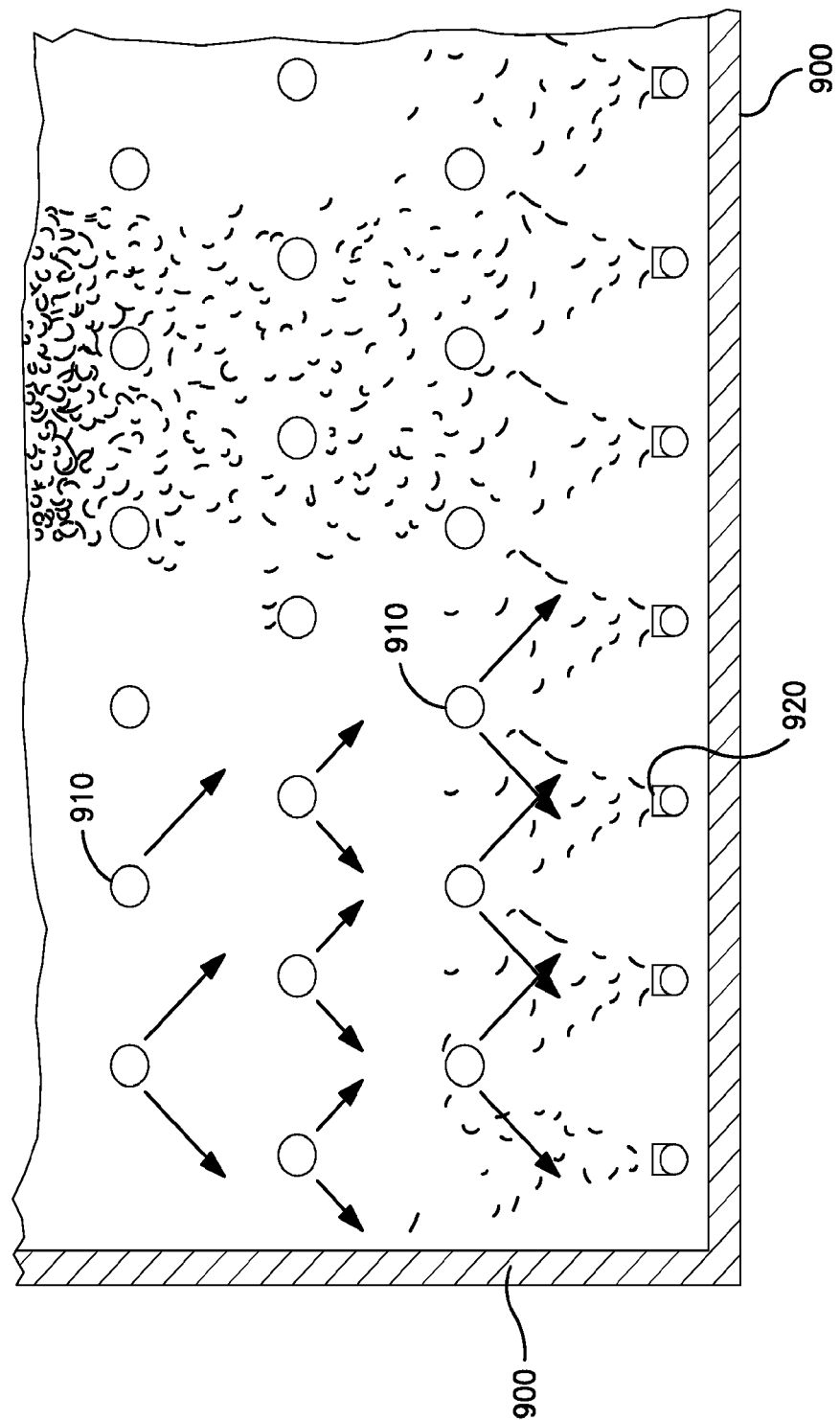
FIG. 30 is a close-up of the cross-sectional view of a portion of the bioreactor shown in FIG. 27.

FIGS. 29 and 30 are partial views of the tanks shown in FIGS. 28 and 27 respectively. With reference to FIG. 29, according to this embodiment of the present invention, the light distributor tubes can conveniently be supplied with light from light sources 950 mounted on one or both sides of the light distributor tubes, as desired. The arrows P in FIG. 30 illustrate light passing from the tubes into the algaeCO$_2$ mixture in the tank.

Figure 31:
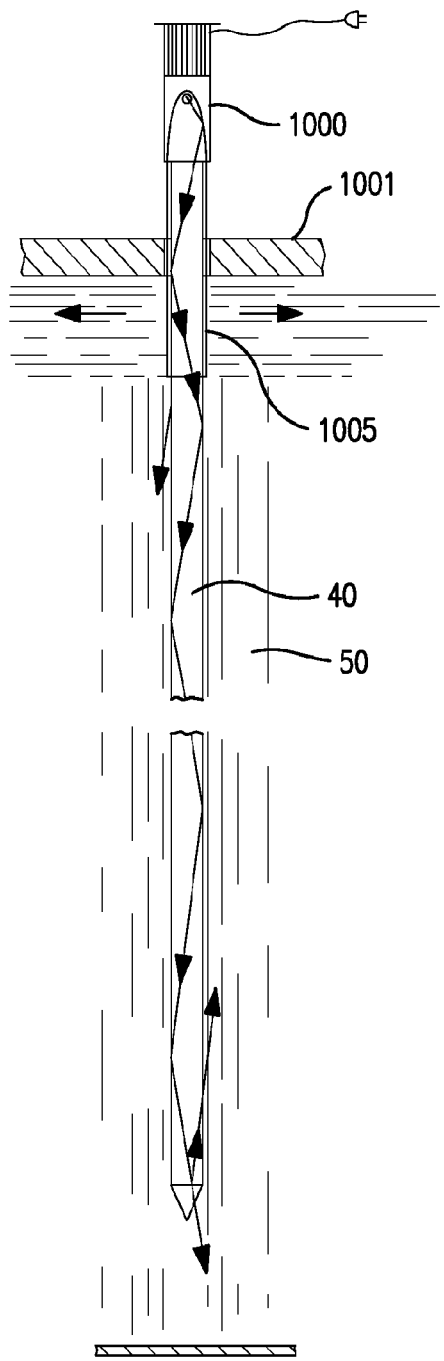
FIG. 31 illustrates an alternative embodiment of the present invention.

FIG. 31 illustrates an alternative embodiment of the present invention wherein an illuminator 1000 is positioned outside the top of a tank 1001 and a rigid tube 1005, for example formed of steel or other durable material, extends partially into the water environment in order to support light distribution tube 40 in water environment 50.

Figure 32:
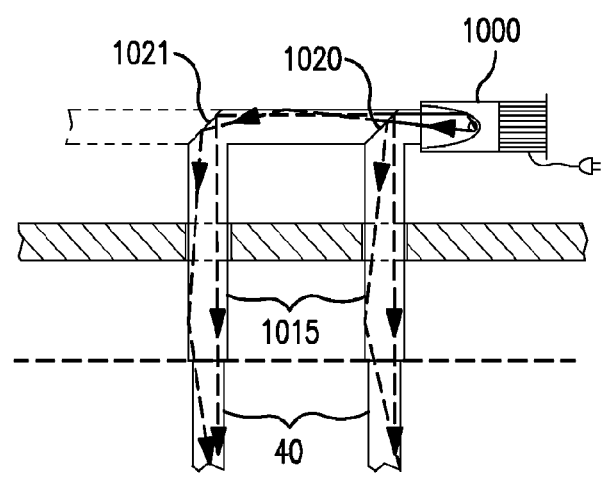
FIG. 32 illustrates a still further embodiment of the present invention wherein a single light source is utilized to illuminate a plurality of tubes.

FIG. 32 is similar to FIG. 31, however, according to this embodiment of the present invention a single illuminator 1000 is connected to a plurality of rigid tubes 1015 and light is directed into tubes 40 utilizing a partially reflective mirror 1020 which directs 50% of the incident light from illuminator 1000 down into right side tube 40 while fully reflective mirror 100 directs 100% of the remaining light down into the tube 40 on the left side of the drawing.

Figure 33:
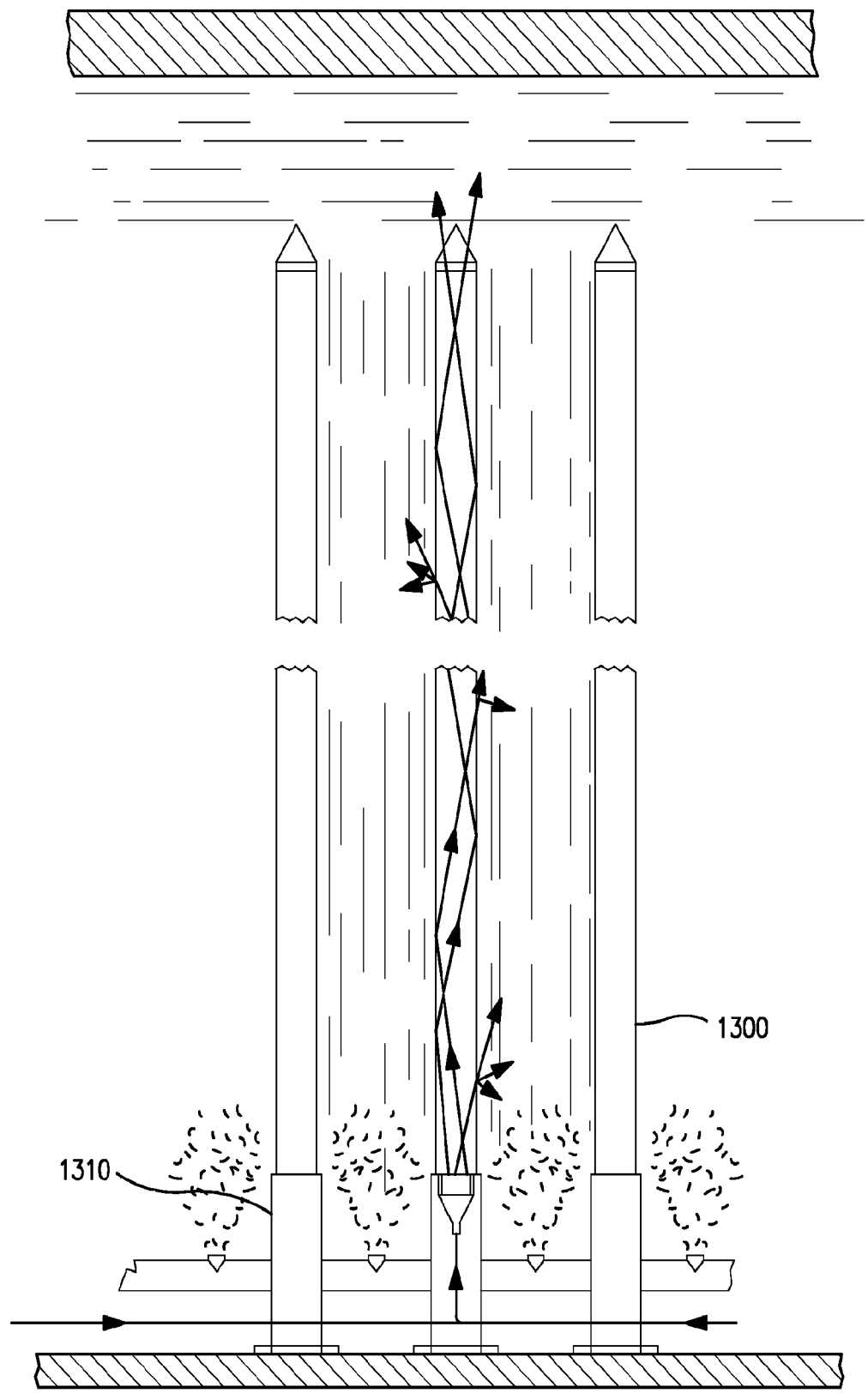
FIG. 33 illustrates an illumination system wherein illumination devices are illuminated from the bottom of a tank.

FIG. 33 illustrates an alternative embodiment of the present invention wherein tubes 1300 are supported at the bottom of a tank. These tubes are also illuminated from the bottom with illuminators 1310.

Figure 34:
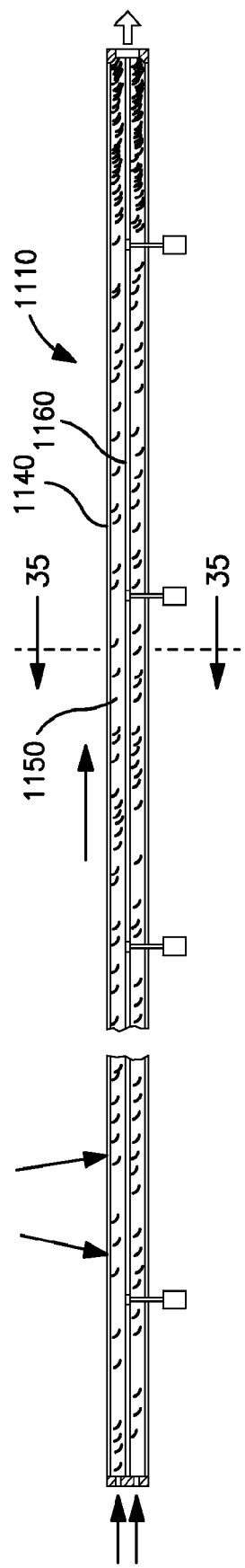
FIG. 34 is a longitudinal sectional view of one embodiment of the present invention.
Figure 35:
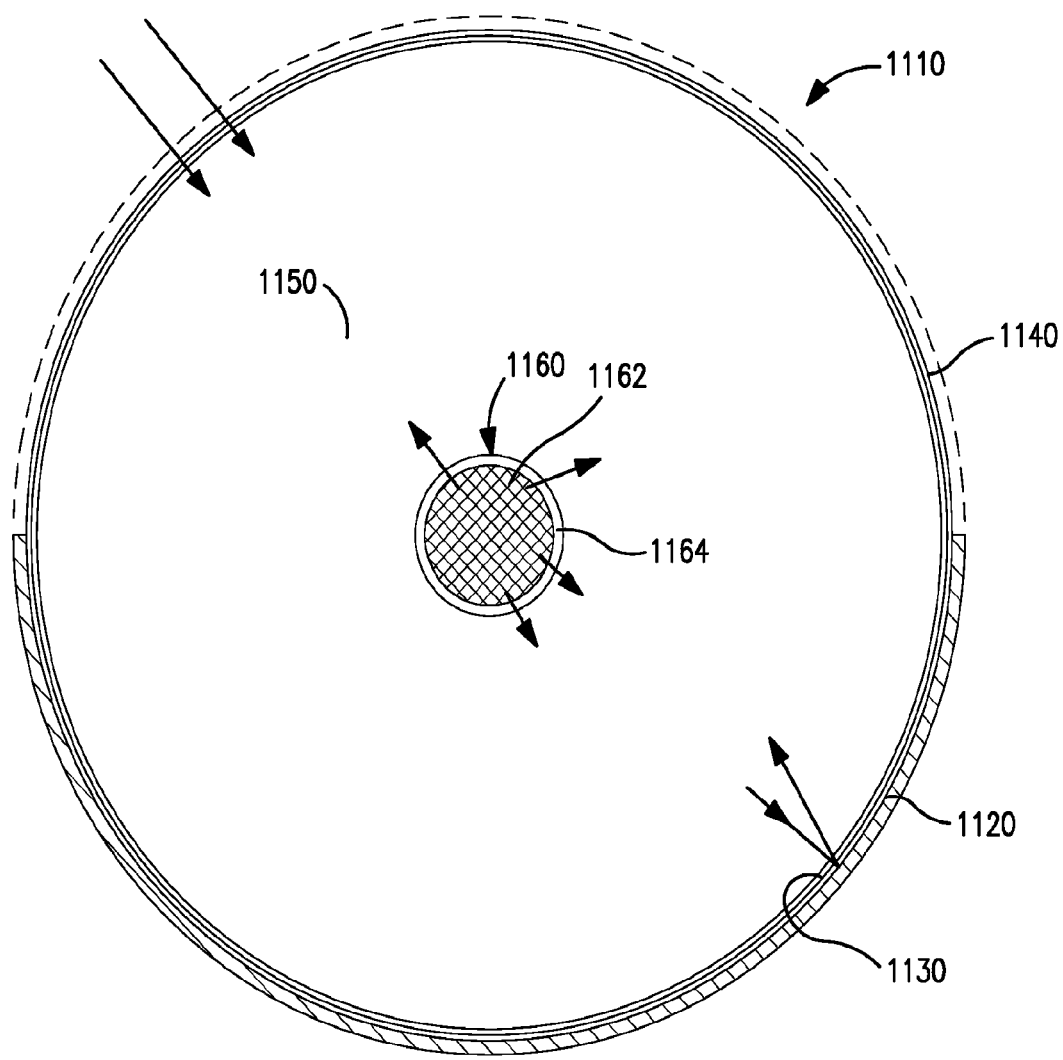
FIG. 35 is a cross-sectional view taken along lines 35-35 of FIG. 34.
Figure 36:
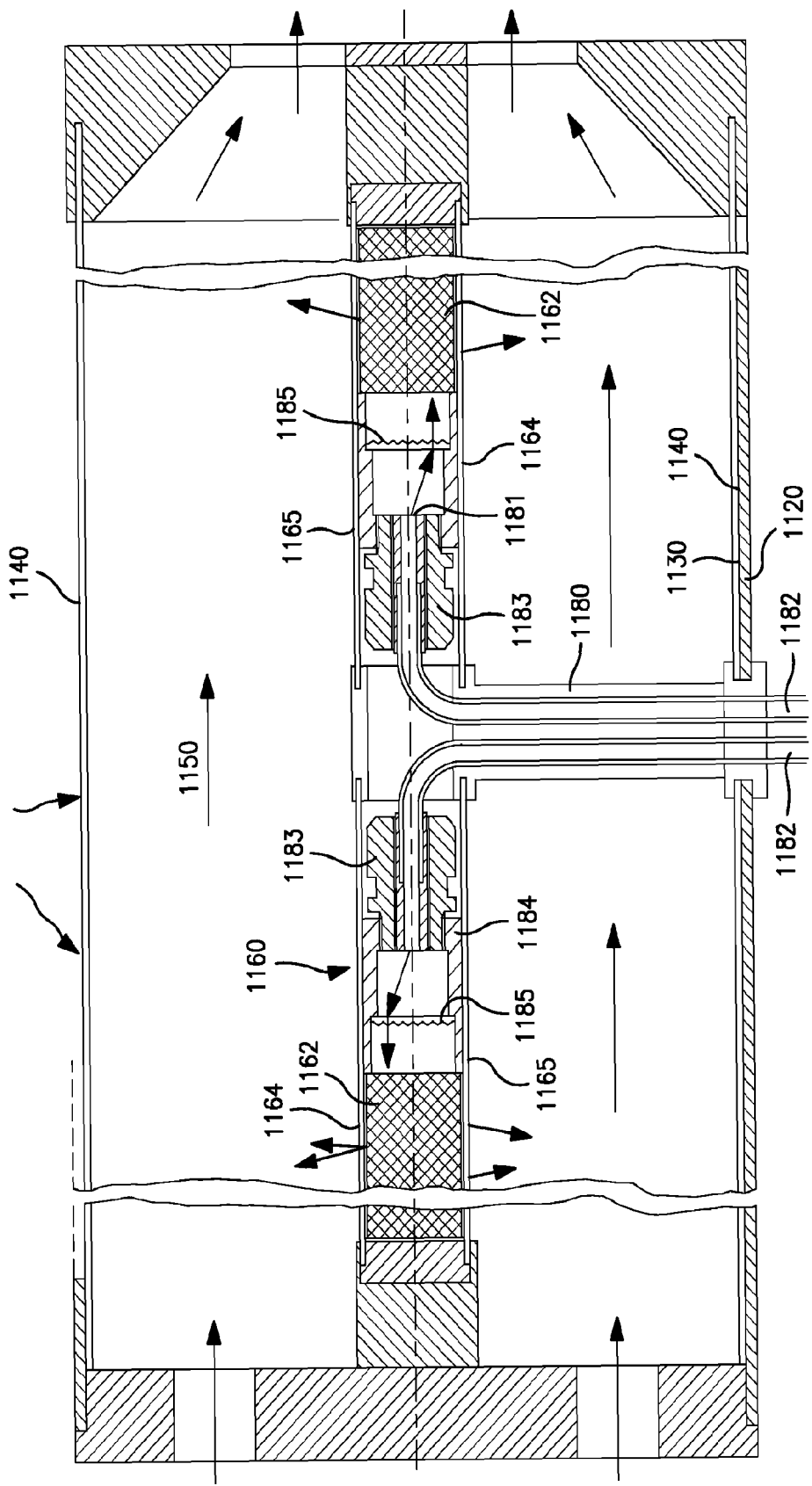
FIG. 36 is close-up view of a portion of FIG. 34.

According to an alternative embodiment shown in FIGS. 34-36, a tubular bioreactor 1110 is supported in a support trough 1120. The interior side of the trough 1120 is provided with a reflective surface 1130, such as a reflective film. The exterior wall 1140 of the bioreactor is at least partially translucent to allow natural sunlight and/or artificial light to pass through the exterior wall(s) and into the interior 1150 for use in the bioreactor, such as for photosynthesis by algae. The interior of outer wall 1140 preferably has low-friction and low-reactivity properties, as well as high light transmission.

According to one preferred embodiment of the present invention, the outer wall comprises PTFE and/or Teflon-FEP which is a fluorinated ethylene propylene (herein after "FEP"). FEP has low-friction properties to reduce the amount of algae growing on the interior walls. Additionally, the interior light distribution source 1160, supports 1180, and wires 1171 (described below) are also preferably coated with a low-friction material and/or a protective, low-friction tube in order to minimize the adherence of algae or other biological organisms which could impede the transmission of light from the interior light source to the desired working area of the bioreactor and/or the flow of algae through the bioreactor. While Teflon-FEP is currently believed to be preferred, other materials can be utilized for the outer (walls) or for covering the inner source of illumination, such as acrylics, polycarbonates, PVC and/or glass.

In FIGS. 35 and 36, it will be understood that the reaction portion 1150 of the tube 1110 is the space between the outer surface of the inner tube 1164 which surrounds the interior light distribution source 1160 and the interior surface of the outer wall 1140. In this illustrated embodiment tubes 1140 and 1160 are formed of FEP or are internally and externally, respectively, coated with FEP or another coating having low friction properties in the bioreactor environment.

The interior light distribution source 1160 is preferably a substantially continuous light distribution tube or non-smooth light emitting rod which emits illumination along substantially the entire length of the light distribution tube or light emitting rod. If a light distribution tube is utilized, it can be a liquid filled light distribution tube such as one of those described above. FIG. 35 illustrates a light emitting rod 1162 comprising a non-smooth cast acrylic rod e.g. scored, etched or grooved, surrounded by an interior tube 1165, e.g. an FEP tube.

FIG. 36 illustrates one method of connecting an exterior source of illumination to light emitting rods 1162. According to this illustrated embodiment, a fiber optic cable 1182 is supplied with illumination from a source (not shown). Fiber optic cable 1182 enters the outer tube 1140 and inner tube 1165 through a support 1180 and then passes into a ferrule 1183 which is connected to a lens housing 1184. Lens housing 1184 supports a Fresnel lens 1185 which collimates light emitted from the distal end 1181 of fiber optic cable 1182. In the embodiment illustrated in FIG. 36, a support 1180 is connected to exterior wall 1140 and interior tube 1165 in order to provide a water tight conduit for fiber optic bundles 1182, as well as to provide positional support for interior tube 1165.

The arrows pointing to the right in the reaction portion 1150 of the bioreactor indicate the flow of algae and/or other organisms or compounds, such as carbon dioxide, which will flow through the tubular reactor.

Figure 37:
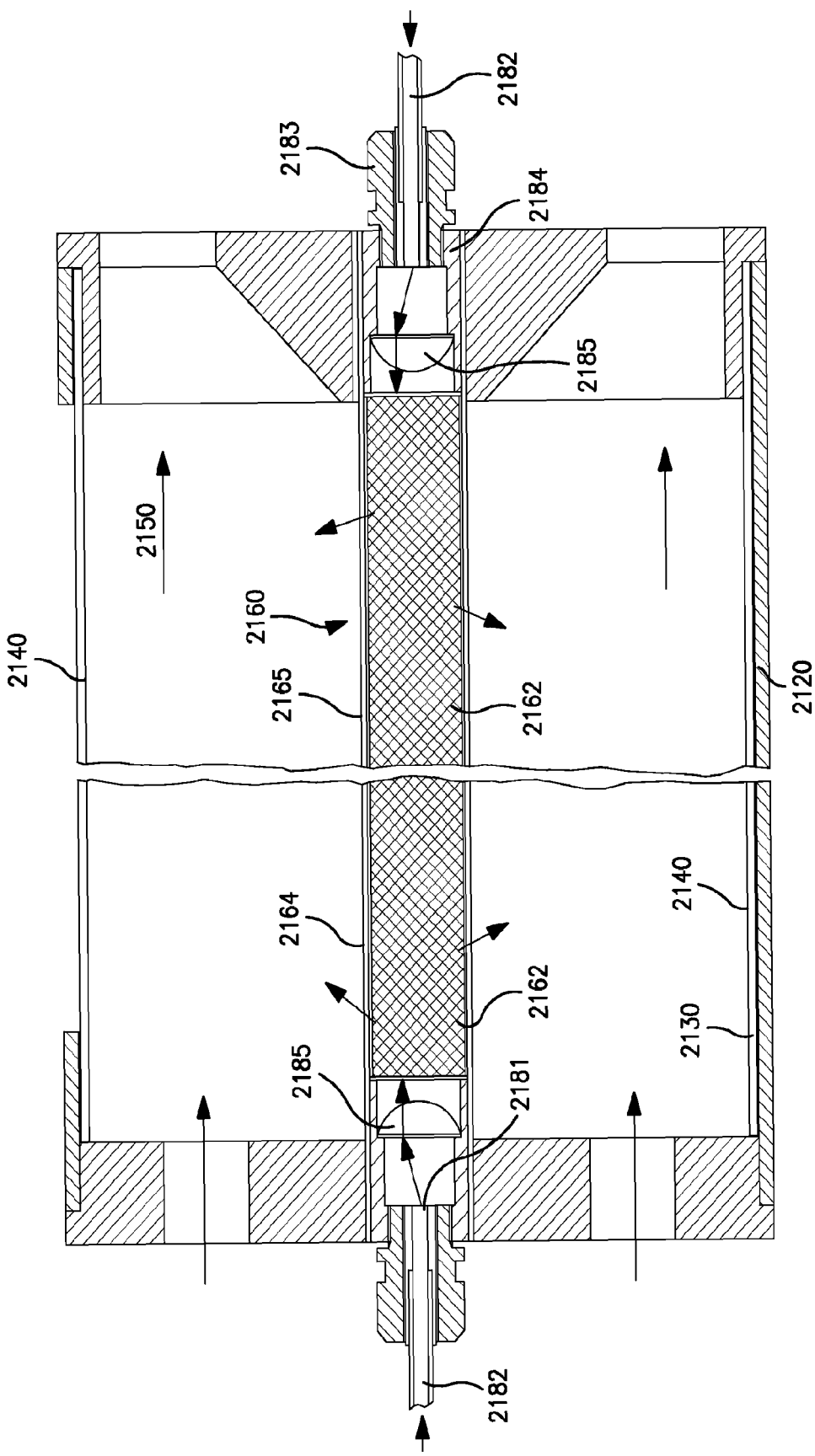
FIG. 37 is close-up view of an alternative embodiment of the present invention.

FIG. 37 illustrates an alternative embodiment of the present invention wherein the interior light distribution source is in the form of a light emitting rod which is illuminated from both ends. The connectors which are positioned at either end of light emitting rod 2162 are similar to those described above in connection with FIG. 36, however instead of using Fresnel lenses, planar-convex lenses 2185 are illustrated. While the embodiment of FIG. 37 illustrates a light emitting rod, it is also within the scope of present invention to use a light distribution tube, e.g. a liquid filled light distribution tube.

Additionally, while each of the illustrated embodiments show a single interior source of illumination, it is within the present invention to use a plurality of elongated light sources which emit light along substantially their entire length.

Figure 38:
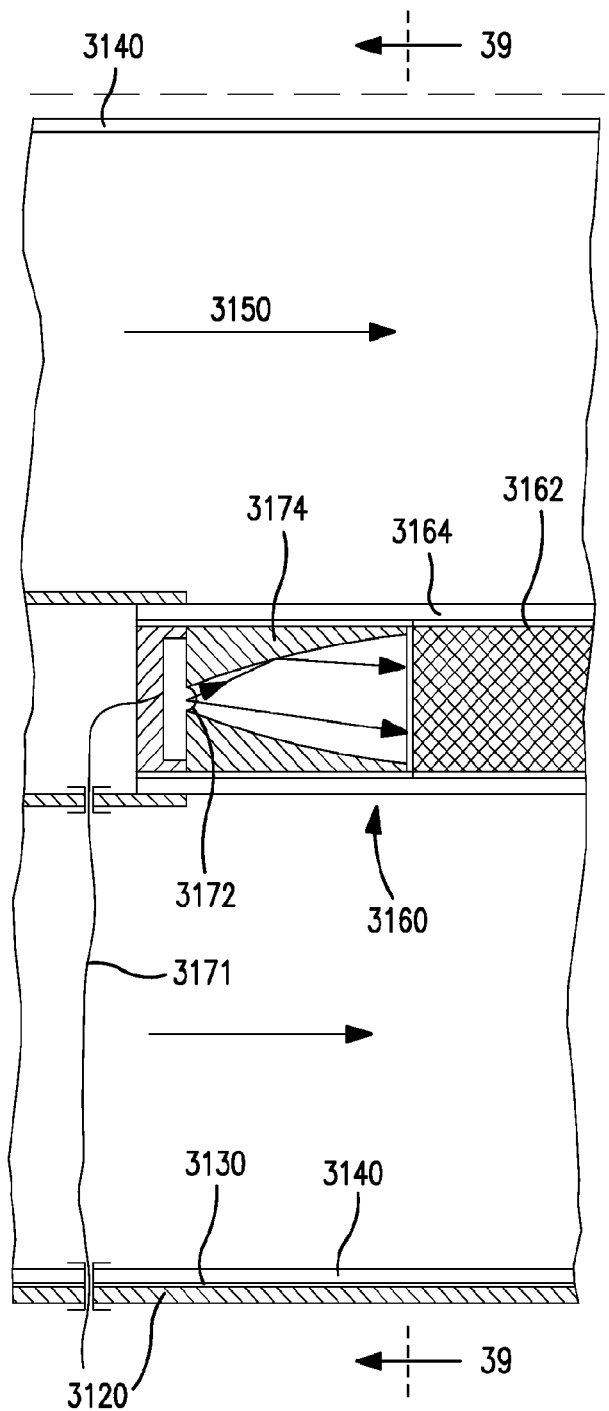
FIG. 38 is a close up view of a portion of further embodiment.
Figure 39:
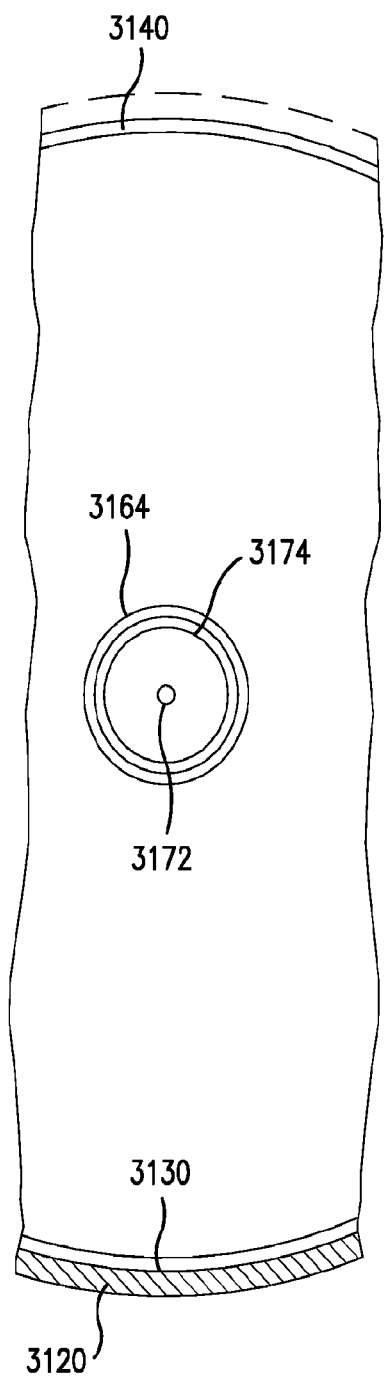
FIG. 39 is a cross-sectional view taken along lines 39-39 of FIG. 38.

FIGS. 38 and 39 illustrate an alternative embodiment of the present invention wherein interior light distribution source 3160 comprises LED 3172 connected to parabolic reflector 3174 which collimates the LED light and directs it into light emitting rod 3162. This embodiment comprises a single LED 3172 within reflector 3174. Rod 3162 and LED 3172 are housed in an outer protective tube 3164, also preferably made of FEP. In this embodiment, electrical wires 3171 provide electrical energy to LED 3172.

FIGS. 40 and 41 illustrate a similar embodiment to that shown in FIGS. 38 and 39, however instead of a single LED 3172 within a single reflector 3174, this embodiment comprises a plurality of LEDs 3272 and a corresponding reflector 3274 for each LED 3272, all of which are housed within a single outer protective tube 3264. While this embodiment illustrates three LEDs, it is also within the scope of the present invention to use a greater number of LEDs to provide either more light or to provide different wavelengths of light. Thus, each of the LEDs can emit light of a different wavelength, if desired.

While the illustrated tubular bioreactors of the present invention have been illustrated in a generally horizontally orientation, it is also within the scope of the present invention to orient the tubular bioreactor vertically or at some intermediate angle. It will also be understood that while the illustrated tubes are cylindrical and have circular cross sections, other cross-sectional shapes can be utilized for the tubes without departing from the scope of the present invention, though generally circular cross-sections are presently deemed preferred.

These tubular bioreactor embodiments of the present inventions provide the advantage of allowing illumination to be provided to the bioreactor from the sun during daylight hours and alternatively or simultaneously to the interior of the reactor either while the sun is not shining such as during the night and/or on cloudy days. Additionally, the ability to illuminate the reaction area of the bioreactor with different light sources such as LEDs, metal halide lamps and plasma lamps provides the ability to separately provide different wave lengths of light and/or different light stimuli such as pulsed light to the bioreactor.

According to another embodiment of the present invention, a tube-within-a-tube bioreactor comprises only an internal light source such as an LDT, liquid filled LDT or LER. Providing an outer wall which is not translucent provides greater control of the light reaching the reaction area of the bioreactor.

The invention claimed is:

1. An illumination system, for Use in a bioreactor comprising a container for a submerged biological medium, said illumination system comprising at least one source of light and a plurality of illumination devices, said illumination devices comprising:
   a light distributing tube having a longitudinal length and at least one sidewall, the sidewall having a first portion and a second portion, where the first portion includes one or more voids within the sidewall which extend substantially longitudinally and cause light incident below a critical angle to be reflected back into the tube, and wherein the second portion is voidless such that projected light above a critical angle that strikes the second portion is transmitted through the sidewall, said tube substantially filled with a liquid.

2. An illumination system according to claim 1 where said light distributing tube comprises an inner tube portion and an outer tube portion.

3. An illumination system according to claim 2 wherein said light distributing tube comprises spacers between said inner and outer tube portions, the spacers forming the voidless second portion.

4. An illumination system according to claim 3 wherein said light distributing tube comprises a plurality of gaps between said spacers, the gaps being the voids that form the first portion.

5. An illumination system according to claim 4 wherein at least some of said gaps comprise air.

6. An illumination system according to claim 4 wherein at least some of said gaps comprise water.

* * * * *